US009629826B2

(12) United States Patent
Gupta

(10) Patent No.: US 9,629,826 B2
(45) Date of Patent: Apr. 25, 2017

(54) CAI-BASED SYSTEMS AND METHODS FOR THE LOCALIZED TREATMENT OF UVEITIS

(71) Applicant: Gen Pharma Holdings, LLC., Pensacola, FL (US)

(72) Inventor: Sunil Gupta, Gulf Breeze, FL (US)

(73) Assignee: GEN PHARMA HOLDINGS, LLC, Pensacola, FL (US)

( * ) Notice: Subject to any disclaimer, the term of this patent is extended or adjusted under 35 U.S.C. 154(b) by 0 days.

(21) Appl. No.: 14/966,067

(22) Filed: Dec. 11, 2015

(65) Prior Publication Data

US 2016/0106718 A1 Apr. 21, 2016

Related U.S. Application Data

(63) Continuation of application No. 14/884,514, filed on Oct. 15, 2015.

(60) Provisional application No. 62/064,815, filed on Oct. 16, 2014.

(51) Int. Cl.
| | | |
|---|---|---|
| *A61K 31/4192* | (2006.01) | |
| *A61K 31/573* | (2006.01) | |
| *A61K 47/48* | (2006.01) | |
| *A61K 9/00* | (2006.01) | |
| *A61K 47/34* | (2017.01) | |
| *A61K 45/06* | (2006.01) | |
| *A61K 47/40* | (2006.01) | |
| *A61K 31/00* | (2006.01) | |

(52) U.S. Cl.
CPC ........ *A61K 31/4192* (2013.01); *A61K 9/0024* (2013.01); *A61K 9/0051* (2013.01); *A61K 31/00* (2013.01); *A61K 31/573* (2013.01); *A61K 45/06* (2013.01); *A61K 47/34* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 4,590,201 A | 5/1986 | Bochis et al. | |
| 4,853,224 A | 8/1989 | Wong | |
| 5,164,188 A | 11/1992 | Wong | |
| 5,378,475 A | 1/1995 | Smith et al. | |
| 5,466,233 A | 11/1995 | Weiner et al. | |
| 5,571,534 A | 11/1996 | Jalonen et al. | |
| 5,602,156 A | 2/1997 | Kohn et al. | |
| 5,679,666 A | 10/1997 | Clark | |
| 5,744,492 A | 4/1998 | Kohn et al. | |
| 5,770,592 A | 6/1998 | Clark | |
| 5,773,019 A | 6/1998 | Ashton et al. | |
| 5,817,075 A | 10/1998 | Giungo | |
| 5,868,728 A | 2/1999 | Giungo et al. | |
| 5,869,079 A | 2/1999 | Wong et al. | |
| 6,120,789 A | 9/2000 | Dunn | |
| 6,217,895 B1 | 4/2001 | Guo et al. | |
| 6,375,972 B1 | 4/2002 | Guo et al. | |
| 6,548,078 B2 | 4/2003 | Guo et al. | |
| 6,726,918 B1 | 4/2004 | Wong et al. | |
| 6,899,717 B2 | 5/2005 | Weber et al. | |
| 7,033,605 B2 | 4/2006 | Wong | |
| 7,276,050 B2 | 10/2007 | Franklin | |
| 7,767,223 B2 | 8/2010 | Wong | |
| 8,034,366 B2 | 10/2011 | Shiah et al. | |
| 8,034,370 B2 | 10/2011 | Shiah et al. | |
| 8,043,628 B2 | 10/2011 | Wong | |
| 8,063,031 B2 | 11/2011 | Wong et al. | |
| 8,088,407 B2 | 1/2012 | Wong | |
| 8,252,307 B2 | 8/2012 | Ashton | |
| 8,506,987 B2 | 8/2013 | Shiah et al. | |
| 8,574,659 B2 | 11/2013 | Guo et al. | |
| 8,614,235 B2 | 12/2013 | Robinson et al. | |
| 8,871,241 B2 | 10/2014 | Chou et al. | |
| 2003/0211144 A1 | 11/2003 | Tabibi et al. | |
| 2004/0033985 A1 | 2/2004 | Chi et al. | |
| 2005/0197637 A1 | 9/2005 | Franklin | |
| 2006/0116404 A1 | 6/2006 | Robinson et al. | |

(Continued)

FOREIGN PATENT DOCUMENTS

| | | |
|---|---|---|
| EP | 1 571 225 A1 | 9/2005 |
| WO | WO-00/037050 A1 | 6/2000 |

(Continued)

OTHER PUBLICATIONS

Amrite et al., "Ocular Distribution of Intact Nano- & MicroParticles Following Subconjunctival & Systemic Routes of Administration," Drug Delivery Technology, Issue Date: vol. 3 No. 2 Mar./Apr. 2003, 8 pages.
Anand, R. et al., "Control of Cytomegalovirus Retinitis Using Sustained Release of Intraocular Ganciclovir," *Arch Ophthamol*, 1993, pp. 223-227, vol. 111.
Angeles Vision Clinic, Angiogenesis Inhibitors for Macular Degeneration, Mar. 23, 2012, printed from http://www.avclinic.com/Angiogenesis.htm, 5 pages.
Antoniotti, S. et al., "Control of Endothelial Cell Proliferation by Calcium Influx and Arachidonic Acid Metabolism: A Pharmacological Approach", *Journal of Cellular Physiology*, 2003, pp. 370-378, vol. 197.
Banker et al., "Modern Pharmaceutics," *Marcel Decker*, 1996, 3rd Edition, 596.
Barisani-Asenbauer et al., "Uveitis—a rare disease often associated with systemic diseases and infections—a systematic review of 2619 patients," *Orphanet Journal Rare Diseases*, 2012, 7: 57-63.

(Continued)

*Primary Examiner* — Layla Berry
(74) *Attorney, Agent, or Firm* — Venable, LLP; Michele V. Frank

(57) ABSTRACT

This invention relates to the treatment of uveitis, in particular posterior infectious uveitis. In specific embodiments, the invention provides for methods of treating uveitis and/or infectious uveitis comprising administration of a sustained-release system containing 5-amino-[4-(4-chlorobenzoyl)-3,5-dichlorobenzyl]-1,2,3-triazole-4-carboxamide) and optionally a glucocorticoid. In one embodiment, the glucocorticoid is dexamethasone. In another embodiment, the sustained-release system comprises a polymer such as e.g. polylactic-coglycolic acid.

21 Claims, No Drawings

(56) References Cited

U.S. PATENT DOCUMENTS

| | | | |
|---|---|---|---|
| 2009/0082288 A1 | 3/2009 | Klinman et al. | |
| 2011/0274748 A1* | 11/2011 | Robinson | A61K 31/4192 424/450 |
| 2014/0079694 A1 | 3/2014 | Robinson et al. | |

FOREIGN PATENT DOCUMENTS

| | | |
|---|---|---|
| WO | WO-01/09106 A1 | 2/2001 |
| WO | WO-2005/107470 A2 | 11/2005 |
| WO | WO-2006/037106 A3 | 3/2006 |
| WO | WO-2006/037106 A2 | 4/2006 |
| WO | WO-2006/037106 R | 12/2006 |

OTHER PUBLICATIONS

Bastin et al., Salt Selection and Optimisation Procedures for Pharmaceutical New Chemical Entities, *Organic Process Research & Development*, 2000 (4), 427-435.

Bauer, K.S. et al., "A Pharmacokinetically Guided Phase II Study of Carboxyamido-triazole in Androgen-independent Prostate Cancer," *Clinical Cancer Research*, 1999, pp. 2324-2329, vol. 5.

Bauer, K.S. et al., "Carboxyamido-triazole Inhibits Angiogenesis by Blocking the Calcium-Mediated Nitric-Oxide Synthase-Vascular Endothelial Growth Factor Pathway," *The Journal of Pharmacology and Experimental Therapeutics*, 2000, pp. 31-37, vol. 292, No. 1.

Benezra et al., "Uveitis in children and adolescents," *Br J Ophthalmol* 2005; 89: 444-448.

Berge et al., "Pharmaceutical Salts," *Journal of Pharmaceutical Sciences*, Jan. 1977, vol. 66, No. 1 pp. 1-19.

Berlin, J. et al., "Phase I and Pharmacokinetic Study of a Micronized Formulation of Carboxyamidotriazole, a Calcium Signal Transduction Inhibitor: Toxicity, Bioavailability and the Effect of Food," *Clinical Cancer Research*, Jan. 2002, pp. 86-94, vol. 8.

Cole K . et al., "Calcium-mediated signal transduction: biology, biochemistry, and therapy." *Cancer Metastasis Rev.* Mar;13(1):31-44, 1994.

Cruysberg, et al., Effective Transscleral Delivery of Two Retinal Anti-Angiogenic Molecules—Carboxyamido-triazole (CAI) and 2-Methoxyestradiol (2ME2), *The Journal of Retinal and Vitreous Diseases*, vol. 24, No. 8, 2005, pp. 1022-1031.

Cunngingham, "Overview of Uveitis," Merck Manuals Professional Edition, Eye Disorders, Oct. 2014, pp. 1-6.

D'Amato, M. et al., "Role of calcium in E-selectin induced phenotype of T84 colon carcinoma cells," *Biochemical and Biophysical Research Communications*, 2003, pp. 907-914, vol. 301.

Faehling, M. et al., "Essential role of calcium in vascular endothelial growth factor A-induced signaling: mechanism of the antiangiogenic effect of carboxyamidotriazole," *The FASEB Journal*, 2002, pp. 1805-1807, vol. 16.

Fahr, A., "Cyclosporin Clinical Pharmacokinetics," *Clin. Pharmacokinet*, 1993, pp. 472-495, vol. 24, No. 6.

Felder C., et al., "The Antiproliferative and Antimetastatic Compound L651582 Inhibits Muscarinic Acetylcholine Receptor-Stimulated Calcium Influx and Arachidonic Acid Release," *Journal of Pharmacology and Experimental Therapeutics*, 1991, pp. 967-971, vol. 257, No. 3.

Figg, W.D., et al., "Pharmacokinetics of Orally Administered Carboxyamido-triazole, an Inhibitor of Calcium-mediated Signal Transduction," *Clinical Cancer Research*, 1995, pp. 797-803, vol. 1.

Final Office Action dated Apr. 15, 2011 in U.S. Appl. No. 11/235,795, 16 pages.

Final Office Action dated Jan. 2, 2013 in U.S. Appl. No. 13/181,847, 16 pages.

Fox, D.A., et al., "Calcium Overload Triggers Rod Photoreceptor Apoptotic Cell Death in Chemical-Induced and Inherited Retinal Degenerations," *Ann N Y Acad Sci.* 1999, pp. 282-285, vol. 893.

Franklin, et al., CAI is a Potent Inhibitor of Neovascularization and Imparts Neuroprotection in a Mouse Model of Ischemic Retinopathy, *IOVS*, Oct. 2004, vol. 45, No. 10, pp. 3756-3766.

Fricker, G. et al., "Permeation enhancement of octreotide by specific bile salts in rats and human subjects: in vitro, in vivo correlations," *Br. J. Pharmacol.*, Jan. 1996, pp. 217-223, vol. 117, No. 1.

Ge, S., et al., "Carboxyamido-triazole Induces Apoptosis in Bovine Aortic Endothelial and Human Glioma Cells," *Clinical Cancer Research*, Apr. 2000, pp. 1248-1254, vol. 6.

Gusovsky, F., et al., "Muscarinic Receptor-mediated Tyrosine Phosphorylation of Phospholipase C-y: An Alternative Mechanism for Cholinergic-induced phosphoinositide breakdown," *The Journal of Biological Chemistry*, 1993, pp. 7768-7772, vol. 268, No. 11.

Hagedorn, M. et al., "Target molecules for anti-angiogenic therapy; from basic research to clinical trials," Critical Reviews in Oncology/Hematology, 2000, vol. 34, No. 2, pp. 89-110.

Hoffmann et al., Carboxyamido-triazole inhibits substeps of choroidal neovascularization on retinal pigment epithelial cells and choroidal endothelial cells in vitro, online Jun. 8, 2004, *Ophthalmologe*. Oct. 2004;101(10):993-7.

Hupe, D.J., et al., "L-651,582 Inhibition of Intracellular Parasitic Protozoal Growth Correlates with Host-Cell Directed Effects," *The Journal of Pharmacology and Experimental Therapeutics*, 1991, pp. 462-467, vol. 156, No. 2.

Hupe et al., "The Inhibition of Receptor-mediated and Voltage-dependent Calcium Entry by the Antiproliferative L-651,582," *The Journal of Biological Chemistry*, 1991, pp. 10136-10142, vol. 266, No. 16.

Hussain, M.M., et al., "Phase II Trial of Carboxyamidotriazole in Patients With Relapsed Epithelial Ovarian Cancer," *The Journal of Clinical Oncology*, Dec. 2003, pp. 4356-4363, vol. 21, No. 23.

Jacobs, W.T., et al., "Inhibitory effects of CAI in glioblastoma growth and invasion," *Journal of Neuro-Oncology*, 1997, pp. 93-101, vol. 32.

Kohn, E.C. et al., "Structure-Function Analysis of Signal and Growth Inhibition by Carboxyamido-triazole, CAI", *Cancer Res.* 54:935-942, 1994.

Kohn, E.C. et al., "In Vivo Efficacy of a Novel Inhibitor of Selected Signal Transduction Pathways Including Calcium, Arachidonate, and Inositol Phosphates", *Cancer Res.* 52:3208-3212, 1992.

Kohn, E.C. et al., "Clinical Investigation of a Cytostatic Calcium Influx Inhibitor in Patients with Refractory Cancers," *Cancer Res.* 56:569-573, 1996.

Kohn, E.C. et al., "Phase I trial of micronized formulation carboxyamidotriazole in patients with refractory solid tumors: pharmacokinetics, clinical outcome, and comparison of formulations." *J Clin Oncol.* 15:1985-1993, 1997.

Kohn, E.C., et al., "Angiogenesis: Role of calcium-mediated signal transduction," *Proc. Natl. Acad. Sci USA.*, Feb. 1995, pp. 1307-1311, vol. 92.

Kohn, E.C., et al., "A phase I Trial of Carboxyamido-triazole and Paclitaxel for Relapsed Solid Tumors: Potential Efficacy of the Combination and Demonstration of Pharmacokinteic Interaction," *Clinical Cancer Research*, Jun. 2001, pp. 1600-1609, vol. 7.

Kohn, E.C., et al., "L651582: A Novel Antiproliferative and Antimetastatic Agent," *Journal of the National Cancer Institute*, Jan. 1990, pp. 54-60, vol. 82, No. 1.

Kohn, E.C., et al., "Calcium Influx Modulates Expression of Matrix Metalloproteinase-2 (72-kDa Type IV Collagenase, Gelatinase A)," *The Journal of Biological Chemistry*, 1994, pp. 21505-21511, vol. 269, No. 34.

Lambert, P.A., et al., "Antiproliferative and antiinvasive effects of carboxyamido-triazole on breast cancer cell lines," *Surgery*, Aug. 1997, pp. 372-379, vol. 122, No. 2.

Ludden, L.K., et al., "Similarity of Metabolism for CAI (NSC 609974) in Human Liver Tissue in Vitro and in Humans in Vivo," *Clinical Cancer Research*, Apr. 1995, pp. 399-405, vol. 1.

Michels et al., Ranibizumab Therapy for Neovascular Age-Related Macular Degeneration, Aug. 1, 2004, printed from http://www.retinalphysician.com/printarticle.aspx?articleI D=1 00004, pp. 9.

Mills, G. et al., "Linking molecular therapeutics to molecular diagnostics: Inhibition of the FRAP/RAFT/TOR component of the P13K pathway preferentially blocks PTEN mutant cells in vitro and in vivo," *PNAS*, Aug. 28, 2001, pp. 10031-10033, vol. 98, No. 18.

Mizutani, M, et al., "Muller cell changes in Human Diabetic Retinopathy," *Diabetes*, Mar. 1998, pp. 445-449, vol. 47.

(56) References Cited

OTHER PUBLICATIONS

Moody, T.W., et al., "CAI inhibits the growth of small cell lung cancer cells," Lung Cancer, 2003, pp. 279-288, vol. 39.
Non-Final Office Action dated Aug. 5, 2010 in U.S. Appl. No. 11/235,795, 15 pages.
Non-Final Office Action dated Mar. 29, 2012 in U.S. Appl. No. 13/181,847, 29 pages.
Oliver, V.K., et al., "Regulation of the Pro-Angiogenic Microenvironment by Carboxyamido-Triazole," *Journal of Cellular Physiology*, 2003, pp. 139-148, vol. 197.
Olson, C. "Ingenuity Abounds as Researchers Explore New Ways of Delivering Medication to Eye," *JAMA*, Dec. 1988, pp. 3556, vol. 260.
Osborne et al., "The potential of neuroprotection in glaucoma in treatment," *Current Opinion Ophthamology*, Apr. 1999, pp. 82-92, vol. 10, No. 2.
Osborne, N.N., et al., "Neuroprotection in Relation to Retinal Ischemia and Relevance to Glaucoma," *Survey of Ophthalmology*, Jun. 1999, pp. S102-S128, vol. 43, Supplement 1.
Pitha et al., "Drug Solubilizers aid pharmacologists: amorphous cyclodextrin derivatives," *Life Sci.*, 1988; 43(6): Abstract only, printed from http://www.ncbi.nlm.nih.gov/pubmed/2841549 on Jul. 31, 2010, 1 page.
Porter, C. J., et al., "Lymphatic transport of halofantrine in the conscious rat when administered as either the free base or the hydrochloride salt: Effect of lipid class and lipid vehicle dispersion," *J. Pharm. Sci.* 85, 357-361, 1996.
Pouton, C. "Lipid formulations for oral administration of drugs: non-emulsifying, self-emulsifying and self-microemulsifying drug delivery systems," *European Journal of Pharmaceutical Sciences*, 2000, pp. S93-598, vol. 11, Suppl. 2.
Read, D.S., et al., "Absence of Voltage-dependent Calcium Channels Delays Photoreceptor Degeneration in rd Mice," *Exp. Eye Res*, 2002, pp. 415-420, vol. 75.
Restriction Requirement dated Oct. 7, 2015 in U.S. Appl. No. 14/083,794, 8 pages.
Rifkin et al., "Recent Developments in the Cell Biology of Basic Fibroblast Growth Factor," *The Journal of Cell Biology*, Jul. 1989, pp. 1-6, vol. 109.
Ryan, S. "The Development of an Experimental Model of Subretinal Neovascularization in Disciform Macular Degeneration," *Tr. Am. Ophth. Soc.*, 1979, pp. 707-745, vol. 77.

Sennlaub, F., et al., "Inducible Nitric Oxide Synthase Mediates Retinal Apoptosis in Ischemic Proliferative Retinopathy," *The Journal of Neuroscience*, May 2002, pp. 3987-3993, vol. 22, No. 10.
Smith Le et al., "Oxygen-induced retinopathy in the mouse." *Invest Ophthalmol Vis Sci.* 35(1):101-11, 1994.
Soltis, M.J., et al., "Identification and Characterization of Human Metabolites of CAI [5-Amino-1-1(4'-Chlorobenzoyl-3,5-Dichlorobenzyl)-1,2,3-Triazole-4-Carboxamide)," *Drug Metabolism and Disposition*, 1996, pp. 799-806, vol. 24, No. 7.
Testa, B., "Prodrug research: futile or furtile?" *Biochemical Pharmacology*, 2004, vol. 68, pp. 2097-2106.
Tutsch, K.D. et al., "Phase I clinical and pharmacokinetic study of rebeccamycin analog (NSC655649)", *Proc Am Assoc Cancer Res.* 37:A1133, 1996.
Vinores, Technology evaluation: pegaptanib, Eyetech/Pfizer, *Curr Opin Mol Ther.* Dec. 2003;5(6), printed from http://www.ncbi.nlm.nih.gov/pubmed/14755895, Abstract, 1 page.
Weckbecker, G. et al., "The Somatostatin Analog Octreotide as Potential Treatment for Re-Stenosis and Chronic Rejection," *Transplantation Proceedings*, 1997, pp. 2599-2600, vol. 29.
Weijtens, O. et al., "Dexamethasone Concentration in the Subretinal Fluid after a Subconjunctival Injection, a Peribulbar Injection, or an Oral Dose," *American Academy of Ophthalmology*, Oct. 2000, pp. 1932-1938, vol. 107, No. 10.
Weijtens, O. et al., "High Concentration of Dexamethasone in Aqueous and Vitreous After Subconjunctival Injection," *Am. J. Ophthalmology*, Aug. 1999, pp. 192-197, vol. 128, No. 2.
Weijtens, O. et al., "Peribulbar corticosteroid injection: vitreal and serum concentrations after dexamethasone disodium phosphate injection," *American Journal of Ophthalmology*, Mar. 1997, pp. 358-363, vol. 123, No. 3.
Weikert et al., "Rapid Ca2+-dependent NO-production from central nervous system cells in culture measured by NO-nitrite/ozone chemoluminescence," *Brain Res*, 1997, pp. 1-11, vol. 748.
Wiedemann, "Drug treatment of ocular neovascularization and proliferation", *Graefe's Archive for Clinical and Experimental Ophthalmology*, May 1999, vol. 237, No. 6, pp. 445-447.
Wu, Y. et al., "Inhibition of Head and Neck Squamous Cell Carcinoma Growth and Invasion by the Calcium influx inhibitor Carboxyamido-triazole," *Clinical Cancer Research*, Nov. 1997, pp. 1915-1921, vol. 3.
International Search Report and Written Opinion, dated Dec. 30, 2015, issued in International Application No. PCT/US2015/055781.

\* cited by examiner

CAI-BASED SYSTEMS AND METHODS FOR THE LOCALIZED TREATMENT OF UVEITIS

CROSS-REFERENCE TO RELATED APPLICATIONS

This application is a continuation of U.S. application Ser. No. 14/884,514, filed Oct. 15, 2015, which claims priority to U.S. Provisional Patent Application No. 62/064,815, filed Oct. 16, 2014, the contents of which are incorporated herein in their entirety.

This application is related to U.S. patent application Ser. No. 14/083,794, filed Nov. 19, 2013, which is a continuation application of U.S. patent application Ser. No. 13/181,847, filed Jul. 13, 2011 (now U.S. Pat. No. 8,614,235, issued Dec. 24, 2013), which is a continuation application of U.S. patent application Ser. No. 11/235,795 (now abandoned), filed Sep. 26, 2005, which claims the benefit of U.S. Provisional Patent Application No. 60/612,683, filed Sep. 24, 2004, each of which are herein incorporated by reference in their entirety.

BACKGROUND OF THE INVENTION 5-amino-1,2,3-triazole-4-carboxamide derivatives were originally discovered as antiparasitic agents and then subsequently demonstrated to be antiproliferative agents and potential cancer therapeutics. The specific compound, 5-amino-[4-(4-chlorobenzoyl)-3,5-dichlorobenzyl]-1,2,3-triazole-4-carboxamide (Formula I illustrated below, shown as the free base form), has been demonstrated to have antiproliferative and antimetastatic activity that was linked to decrease of intracellular calcium by inhibition of non-voltage-gated calcium channels. It is an inhibitor of trans-membrane calcium influx and intracellular calcium requiring signalling pathways. Tyrosine kinase and metalloproteinase pharmacological mechanistic activities and anti-angiogenesis activity relevant to antitumor efficacy have also been described for this compound. The compound of Formula I will be referred to in the following discussion using the acronym CAI (carboxy-amido-triazole) which is generally used to describe the compound.

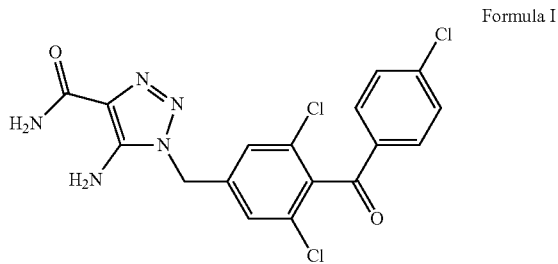 [SMILES: NC(=O)c1nnn(Cc2cc(Cl)c(C(=O)c3ccc(Cl)cc3)c(Cl)c2)c1N]

Formula I

Clinical investigations have been conducted with CAI in the treatment of life-threatening diseases. For example, CAI has been used in the treatment of a variety of refractory tumors, including prostate cancer, lymphomas, glioblastoma, peritoneal cancer, fallopian tube cancer, epithelial ovarian cancer, advanced renal cell carcinoma, metastatic renal carcinoma, and non-small cell lung cancer (Bauer, K. S. et al. *Clin Cancer Res.* 5:2324-2329, 1999; Kohn, E. C. et al. *Cancer Res.* 52:3208-3212, 1992; Kohn, E. C. et al. *J Biol Chem.* 269:21505-21511, 1994; Kohn, E. C. et al. *Proc Natl Acad Sci USA.* 92:1307-1311, 1995; Kohn, E. C. et al. *Cancer Res.* 56:569-573, 1996; Kohn, E. C. et al. *J Clin Oncol.* 15:1985-1993, 1997; Kohn, E. C. et al. *Clin Cancer Res.* 7:1600-1609, 2001.

While these studies using CAI indicate that CAI has intrinsic clinical efficacy for many cancer types, the systemic oral dosage regimens and formulations used in a clinical setting to date have been associated with dose limiting side effects. Moreover, toxic effects (cerebellar ataxia, peripheral neuropathy and exacerbation of depression) have been observed in clinical studies at doses of CAI required to achieve circulating levels that are within a narrow range or those projected from pharmacological studies to be required for effective inhibition of pathological neovascularization. Furthermore, a serious side effect associated with clinical use of CAI by systemic administration has been the loss of vision for which two cases have been described (Berlin, J. et al. *Clin Cancer Res.* 8:86-94, 2002). Therefore, use of CAI as currently applied in clinical investigations for cancer is effectively precluded for acute or chronic treatment of non-life threatening conditions, in particular for the treatment of ocular diseases described herein.

To treat certain ocular diseases, such as age-related macular degeneration (or ARMD), and diabetic retinopathy, or diseases with specific ocular manifestations, such as von Hippel landau syndrome, therapeutic treatments rely on occlusion of the blood vessels using either threshold laser photocoagulation, or subthreshold laser combined with a photoactivated dye. However, such treatment requires either full-thickness retinal damage by thermal destruction, or damage to medium and large choroidal vessels thereby precluding any potential visual recovery. Further, the subject is left with a scar and visual scotoma. Moreover, recurrences are common, and visual prognosis is poor.

Recent research in the treatment of neovascularization has had the aim of causing a more selective closure of the blood vessels, in order to preserve the overlying neurosensory retina. Such strategies have been used for the treatment of diabetic retinopathy, the leading cause of blindness among working age adults in Europe and the United States. However, extensive ocular tissue damage can occur after pan-retinal photocoagulation, with the visual handicap of more limited peripheral vision and poor night vision. With focal laser treatment, photocoagulation often can further compromise macular blood flow. Alternatively, a variety of molecules are in development or have been approved that target angiogenic pathways (e.g. the VEGF pathway). Thus, using antiangiogenic compounds is an alternative to lasering of patients.

CAI is an anti-angiogenic and anti-parasitic compound; however, the poor aqueous solubilities of CAI compounds, as well as reported neurotoxicity for CAI, means that novel methods of administration and targeted administration of CAI compounds are required for providing safe and effective doses to treat disease and non-life threatening diseases in particular.

High local concentrations of CAI may be required to treat acute disease symptoms while lower concentrations can be effective as continuation therapy or prophylactic therapy. Additionally the frequency of administration of a formulation of a CAI compound can also be used to ensure safe and effective local concentrations to slow vascular outgrowth. Treatment may be necessary from every week, to every month to few months, to yearly dosing with appropriate molecules in sustained delivery systems.

Posterior segment neovascularization (NV) is the vision-threatening pathology responsible for the two most common causes of acquired blindness in developed countries: exudative ARMD and proliferative diabetic retinopathy (PDR). Currently the only approved treatments for posterior segment NV that occurs during exudative ARMD are laser photocoagulation, photodynamic therapy with VISUDYNE®, and the VEGF binding oligonucleotide aptamer Macugen®. Laser and photodynamic therapies involve occlusion of affected vasculature, which results in localized laser-induced damage to the macula. For patients with PDR, surgical interventions with panretinal laser, or vitrectomy and removal of preretinal membranes, or treatment with Macugen® are the only treatment options currently available. However, in addition to the recently approved anti-VEGF aptamer oligonucleotide Macugen®; several different compounds are being evaluated clinically, including, for example, anecortave acetate (Alcon Research, Ltd.), and Lucentis® (ranibizumab, Genentech), Squalamine lactate (Genaera Corporation), LY333531 (Lilly), Cand5 (Acuity Pharmaceuticals), Talaporfin sodium (Light Sciences Corp.), and Fluocinolone (Bausch & Lomb).

Treatments using dosage regimens, routes of administration and formulations of CAI described to date do not have adequate safety for treating severe proliferative diseases that are non-life threatening. There exists an unfulfilled need for new dosage regimens, routes of administration and formulations of CAI that can provide therapeutic effects on non-life threatening proliferative diseases, as exemplified by ocular diseases that are characterized by neovascularization and pathological cellular proliferation and invasion. There also exits an unfilled need for administering CAI formulations that can provide therapeutic effects on uveitis, which is characterized by the swelling of the middle layer of the eye and which according to Barisani-Asenbauer et al. "is the fourth most common cause of blindness among the working-age population in the developed world." *Orphanet Journal of Rare Diseases* 2012, 7:57.

BRIEF SUMMARY OF THE INVENTION

The subject invention provides novel sterile aqueous formulations of CAI compounds, their use in the localized treatment of ocular diseases, as well as methods for their manufacture. In some embodiments of the invention, novel and advantageous CAI compounds, their respective formulations, and methods for their use are provided. The novel CAI compounds and aqueous, sterile formulations of the invention are particularly useful in the localized treatment of non-life threatening diseases such as proliferative diseases, ocular diseases or conditions, inflammatory conditions, edematous diseases, signal transduction-mediated diseases, and matrix metalloproteinase-mediated diseases, and neovascular diseases. In particular, the novel CAI compounds and aqueous, sterile formulations of the invention when used in a sustained release system are useful for the treatment of uveitis and especially posterior infectious uveitis.

In certain embodiments, CAI compounds of the present invention are crystalline and small particulate pure free base forms of CAI, CAI prodrugs, and CAI acid addition salt forms. Further embodiments of the invention provide novel, therapeutically effective formulations of crystalline and small particulate pure free base forms of CAI compounds of the invention. In other embodiments, the CAI compounds of the claimed invention are provided as sonicated microparticles or in a complex, such as e.g. in complex with beta-cyclodextrin. When formulated as microparticles or complex, the CAI compounds may be further used with time-release delivery systems.

Specific diseases that can be treated with the CAI compounds of the invention include, but are not limited to, ocular disease including neovascular ocular disease, edematous ocular disease, ocular tumors, and intraocular inflammation; dermatological disease including psoriasis, eczema, actinic keratosis, and rosacea; inflammatory disease including arthritis and arthrosis; neurological diseases including neurodegenerative disease, pain, and epilepsy; cancers including cancers of the bladder, brain, breast, colon, endometria, kidney, lungs, pancreas, and thyroid; and proliferative vascular disorders including restenosis or proliferation associated with angioplasty. Such diseases include, but are not limited to, uveitis (anterior uveitis, intermediate uveitis, posterior uveitis and diffuse uveitis). In one embodiment, the CAI compounds of the invention may be used to treat posterior uveitis, such e.g. posterior infectious uveitis. In yet another embodiment, the CAI compounds of the invention may be used to treat posterior infectious uveitis caused by toxoplasmosis, *toxocara* and visceral larva migrans or other parasitic diseases.

Aqueous, sterile formulations as described herein provide for the localized administration of high concentrations of CAI compounds (which are normally poorly soluble) for the treatment of such acute therapeutic indications as exemplified by severe neovascular ocular disease stages of "wet" ARMD or diabetic retinopathy. Similarly, for chronic use, the subject invention provides sterile, aqueous formulations for the controlled release of CAI compounds via oral, systemic or local routes of administration, where such formulations ensure the maintenance of therapeutic CAI compound drug levels with low variability and reliability for chronic application.

Treating localized proliferative diseases, including those characterized by neovascular pathology, by the local administration of CAI compounds of the invention as described herein, provides significant advantages to the systemic administration of CAI with such systemic administration having been practiced in cancer to date.

Local administration of CAI compounds as provided herein allows for the maintenance of efficacious, non-toxic levels of active CAI free drug at the local tissue disease site, thus providing a high margin of safety and enables therapeutically effective treatment of diseases, particularly non-life threatening diseases. The localized treatment of non-life threatening diseases using CAI compounds as described herein provides significant advantages relative to systemic treatment with forms and formulations of CAI described to date, which have unacceptable low safety thresholds.

Similarly, according to the subject invention, the local administration of CAI compounds, and formulations thereof, by means of a drug delivery device or implant placed in proximity to the local tissue site provides for the maintenance of efficacious, safe levels of active CAI drug ingredient at the local tissue disease site. Thus, the subject invention provides a high margin of safety and enables use in treating non-life threatening diseases for which CAI dosed systemically, in forms described to date, is practically precluded.

In one embodiment, local administration of CAI compounds as described herein is suitable for acute disease therapy and induction of remission of disease signs and symptoms. In another embodiment, local administration of CAI compounds as described herein is suitable for chronic disease therapy and maintenance of remission of disease signs and symptoms.

According to the subject invention, the local ocular administration of CAI compounds of the invention, and/or formulations thereof, attenuate ocular pathological disease processes without unduly compromising normal healthy ocular function. Thus, local ocular administration of a CAI compound of the invention, and/or formulations thereof, provides for an efficacious but safe controlled concentration range of CAI directly in the eye.

Ocular CAI-based therapies, as describe herein, provide significant advantages for treating neovascular ocular disease relative to current laser surgery treatment modalities including panretinal photocoagulation, which can be accompanied by extensive ocular tissue damage. In the examples of posterior neovascular ocular diseases, such as Age-related Macular Degeneration and Diabetic Retinopathy, target ocular pathologies and tissues for treatment are especially localized to the retinal, choroidal and corneal ocular compartments.

It is contemplated herein that CAI compounds of the invention can readily penetrate the human scleral tissue after periocular administration in patients with ocular disease. This particular property of CAI compounds and CAI-based formulations of the invention enables effective minimally invasive delivery of the parent CAI therapeutic entity (or also referred to herein as CAI free base) to the patient's diseased ocular tissue compartment(s) in therapeutic concentration without causing ocular toxicity that has been previously observed with the systemic administration of the biologically active CAI parent drug to cancer patients.

According to the subject invention, tissue targets for localized treatment using the CAI compounds include, but are not limited to, dermal, ocular, pulmonary, vascular, joint, nasal, ictic, bone, gastrointestinal, and localized neural tissues e.g. brain and spinal column of the central nervous system. Accordingly, administrations of CAI compounds of the invention as described herein can be used to treat ocular, dermatological, pulmonary, vascular, joint, bone, nasal, ictic, gastrointestinal and neurological diseases. In a one embodiment, CAI compounds of the invention, and/or formulations thereof, are useful for treating local disease pathologies that are targeted by the established pharmacological mechanism(s) of action of CAI to inhibit the pathological increase in intracellular calcium concentration that blocks hyperproliferative, inflammatory, neurodegenerative, edematous, macroscopic pathologies associated with localized target diseases described herein. In another embodiment, the CAI compounds of the invention, and/or formulations thereof, are useful for treating local disease pathologies associated with inflammation due to the presence of parasites (such as e.g. *Toxoplasma gondii*) in the eye.

In an alternate embodiment, the present invention provides CAI compounds and CAI compound formulations that provide for controlled release of pharmacologically active CAI in a targeted tissue and at therapeutically effective concentrations. Such CAI compounds can be locally delivered or administered to a target tissue in vivo by passive spontaneous, biologically accelerated, or assisted (such as sonophoresis or galvanic, e.g. iontophoresis) mechanisms.

The CAI compounds of the present invention and formulations thereof, are advantageous because they overcome problems associated with sterility, stability, toxicity, lack of target tissue specificity, safety, efficacy, extent, and variability of bioavailability, which exist with the administration of the active form of CAI. The CAI compounds of the present invention, and CAI compound formulations, are particularly advantageous in minimizing the undesirable side effects associated with current CAI treatment or therapy, such as loss of vision, cerebellar ataxia, peripheral neurotropathy, and exacerbation of depression.

As contemplated in the subject invention, where a CAI compound comprises a CAI prodrug, the CAI prodrug can be converted to a biologically active CAI compound at a controlled rate via passive (such as by aqueous hydrolysis) or biologically mediated (such as biocatalytic or enzymatic, e.g. by intraocular esterases) mechanisms. An advantage of the in vivo conversion of the CAI-based prodrug to CAI is that the ensuing CAI provides localized therapeutic effects in target disease tissue with high therapeutic margins of safety.

A further embodiment provides the use of CAI compounds in conjunction with a drug delivery system in the form of an implant or a device for the treatment of conditions as set forth herein. Certain embodiments of the invention contemplate the use of CAI compounds and formulations thereof for use comprising a coating for example of a device in conjunction with physical device implants such as stents and band ligatures. Therapeutic uses of such implants include but are not limited to vascular diseases such as restenosis, and in bone and tissue grafts.

A further embodiment of the subject invention provides for the local administration of CAI compounds in combination with other pharmacological therapies. As contemplated in the subject invention, combination therapies of CAI compounds with other medicaments targeting similar or distinct disease mechanisms have advantages, which include greater efficacy in therapeutic treatment of a disease and greater margins of safety relative to respective monotherapies with either specific or separate medicament.

In one embodiment, a CAI compound is used in a method to treat neovascular ocular disease comprising localized (for example, in ocular tissue) concurrent administration with one or more other medicaments each of which may act to block angiogenesis by a pharmacological mechanism. Such combinations would act by providing for superior efficacy from mechanisms of action from additivity, synergy, or amelioration of side effects. Medicaments that can be concurrently administered with a CAI compound of the invention include, but are not limited to, vascular endothelial growth factor VEGF blockers (e.g. by VEGF neutralizing binding molecules such as Macugen® (Eyetech) and Lucentis® (ranibizumab, Genentech), Squalamine lactate (Genaera Corporation); and VEGF tyrosine kinase inhibition) for treating neovascular ocular disease (ARMD and Diabetic Retinopathy) and glucocorticoids (e.g. Triamcinolone) for treating macular edema. Other growth factors that can be concurrently administered with the CAI compounds of the invention (preferably in sterile, aqueous formulations) include, but are not limited to, Pigment Epithelium Derived Factor (PEDF), Erythropoietin (EPO), integrin, endostatin, R-cadherin, angiostatin, and fibroblastic growth factor.

The systems and method may include treatment of uveitis with CAI compounds alone or as part of combination therapy. In particular, in certain embodiments of the invention, CAI may be used in a time-release formulation to treat posterior infectious uveitis.

In certain embodiments, the invention provides for using a CAI compound such as e.g. 5-amino-[4-(4-chlorobenzoyl)-3,5-dichlorobenzyl]-1,2,3-triazole-4-carboxamide) in the treatment of uveitis, in particular posterior infectious uveitis. When used to treat uveitis (e.g. posterior infectious uveitis), the CAI compound may be used in conjunction with any of the other optional components described herein such as antibacterial agents and/or anti-inflammatory agents. In certain embodiments, the CAI compound alone or conjunction with other components is administered in a time-release formulation such as e.g. a sustained release system. Accordingly, one embodiment of the invention is a method of treating uveitis including administering a sustained-release system containing a pharmaceutically effective amount of 5-amino-[4-(4-chlorobenzoyl)-3,5-dichlorobenzyl]-1,2,3-triazole-4-carboxamide) and optionally a glucocorticoid to a patient. Thus, in one embodiment of the invention, the method includes administration of a sustained-release system containing a pharmaceutically effective amount of 5-amino-[4-(4-chlorobenzoyl)-3,5-dichlorobenzyl]-1,2,3-triazole-4-carboxamide). In other embodiments, the method includes administering a sustained-release system containing a pharmaceutically effective amount of 5-amino-[4-(4-chlorobenzoyl)-3,5-dichlorobenzyl]-1,2,3-triazole-4-carboxamide) and a glucocorticoid to a patient. The method may also include diagnosing uveitis in the patient. In certain embodiments, the sustained-release formulation may include a polymer such as e.g. polylactic-coglycolic acid (PLGA). In one embodiment, the polymer is poly (D,L-lactide-co-glycolide) PLGA.

While a variety of glucocorticoids may be used, in one embodiment, the glucocorticoid may be dexamethasone such as e.g. from about 0.5 to about 0.9 mg of dexamethasone. The sustained-release system may include additional components including an anti-inflammatory agent and/or an antibacterial agent. The sustained-release system may be administered by intravitreal injection or intravitreal implantation. In one embodiment, the sustained-release system includes poly (D,L-lactide-co-glycolide) PLGA and dexamethasone. In one particular embodiment, the sustained-release system includes an OZURDEX® (dexamethasone) intravitreal implant.

In another embodiment, the invention provides for methods of treating infectious uveitis. The method includes administering a sustained-release system containing a pharmaceutically effective amount of 5-amino-[4-(4-chlorobenzoyl)-3,5-dichlorobenzyl]-1,2,3-triazole-4-carboxamide) and optionally glucocorticoid to a patient. Accordingly, in one embodiment, the method includes administering a sustained-release system containing a pharmaceutically effective amount of 5-amino-[4-(4-chlorobenzoyl)-3,5-dichlorobenzyl]-1,2,3-triazole-4-carboxamide) and glucocorticoid to a patient. The method may also include diagnosing posterior infectious uveitis in the patient. In certain embodiments, the sustained-release formulation includes a polymer. In one embodiment, the polymer contains polylactic-coglycolic acid (PLGA). In one specific embodiment, the polymer is poly (D,L-lactide-co-glycolide) PLGA. In certain embodiments, in methods in which a glucocorticoid is used, the glucocorticoid includes or is dexamethasone. In certain embodiments, the sustained-release system contains from about 0.5 to about 0.9 mg of dexamethasone. In other embodiments, the sustained release system contains from about 150 mcg to about 200 mcg of 5-amino-[4-(4-chlorobenzoyl)-3,5-dichlorobenzyl]-1,2,3-triazole-4-carboxamide). The sustained-release system may contain a variety of additional components. In one embodiment, the sustained-release system include an anti-inflammatory agent and/or an antibacterial agent. The method may include various routes of administration. In certain embodiments, the methods include intravitreal injection or implantation. In one embodiment, the method for treating posterior infectious uveitis includes administration of a sustained-release system containing poly (D,L-lactide-co-glycolide) PLGA, dexamethasone and 5-amino-[4-(4-chlorobenzoyl)-3,5-dichlorobenzyl]-1,2,3-triazole-4-carboxamide). The sustained-release system may be an implant. In one particular embodiment, the sustained-release system is an OZURDEX® (dexamethasone) intravitreal implant to which 5-amino-[4-(4-chlorobenzoyl)-3,5-dichlorobenzyl]-1,2,3-triazole-4-carboxamide) has been added.

The invention also generally provides for methods of treating uveitis by administering a sustained-release system containing a pharmaceutically effective amount an anti-parasitic or anti-bacterial agent and a glucocorticoid to a patient. The method may also include diagnosing uveitis in the patient. The sustained-release formulation may contain a polymer. In certain embodiments, the polymer includes polylactic-coglycolic acid (PLGA). In one embodiment, the polymer includes poly (D,L-lactide-co-glycolide) PLGA. In one embodiment, the uveitis is posterior infectious uveitis. The anti-parasitic agent may be 5-amino-[4-(4-chlorobenzoyl)-3,5-dichlorobenzyl]-1,2,3-triazole-4-carboxamide).

The glucocorticoid may be dexamethasone. In some embodiments, the sustained-release system contains from about 0.5 to about 0.9 mg of dexamethasone. The sustained-release system may also further contain an anti-inflammatory agent. The step of administration may include intravitreal injection and/or implantation. In one embodiment, the sustained-release system includes poly (D,L-lactide-co-glycolide) PLGA and dexamethasone. Thus, the sustained-release system may include an OZURDEX® (dexamethasone) intravitreal implant.

In one embodiment, the invention provides for a method of treating uveitis in a patient by administering a sustained-release system comprising a pharmaceutically effective amount of 5-amino-[4-(4-chlorobenzoyl)-3,5-dichlorobenzyl]-1,2,3-triazole-4-carboxamide) (CAI). In one embodiment, the uveitis is posterior infectious uveitis, which in certain embodiments may caused by toxoplasmosis, *toxocara* or visceral larva migrans. The sustained release-system may be a polymer, which may degrade over time. In certain embodiments, the polymer may be polylactic-coglycolic acid (PLGA) such as poly (D,L-lactide-co-glycolide) PLGA. In other embodiments, the sustained release system may be a non-erodible intravetreal implant. The sustained-release system further includes one or more of an anti-inflammatory agent, a steroid and/or an antibacterial agent. In certain embodiments, the steroid is a glucorticoid (such as e.g. dexamethasone) or fluocinolone acetonide. In one embodiment, the sustained-release system may from about 0.5 to about 0.9 mg of dexamethasone. The sustained release system may administered by a variety of routes including but not limited to intravitreal injection and intravitreal implantation. In one embodiment, the sustained-release system contains poly (D,L-lactide-co-glycolide) PLGA and dexamethasone. The sustained-release system is an implant. When used as part of a sustained release system, CAI may be provided in a variety of different formulations. For example, CAI may be provided as a sonicated microparticle or in a molecular complex in formulation with hydroxypropyl β-cyclodextrin. In certain embodiments, CAI is in a molecular complex formulation with 1 to 60 wt % hydroxypropyl β-cyclodextrin and one or more of glutamate, L-phenylalanine, a cellulose derivative (such as e.g. hydroxypropyl methyl cellulose), and a surfactant. The sonicated CAI microparticle or CAI molecular complex may have a diameter of less than 10 micrometers. The sustained-release system may include an OZURDEX® (dexamethasone) intravitreal implant or an ILUVIEN® (fluocinolone acetonide) intravitreal implant.

Another embodiment of the invention is a method of treating posterior infectious uveitis (such as e.g. posterior infectious uveitis caused by toxoplasmosis, *toxocara* or visceral larva migrans) in a patient comprising administering a sustained-release system comprising a pharmaceutically effective amount of 5-amino-[4-(4-chlorobenzoyl)-3,5-dichlorobenzyl]-1,2,3-triazole-4-carboxamide) and a steroid to a patient. In certain embodiments, the steroid is a glucocorticoid or fluocinolone acetonide. The sustained-release system may be a polymer such as for example, polylactic-coglycolic acid (PLGA) (e.g. poly (D,L-lactide-co-glycolide) PLGA). The polymer may degrade over time. The steroid may be dexamethasone. In certain embodiments, the sustained-release system contains from about 0.5 to about 0.9 mg of dexamethasone. In other embodiments, the sustained-release system also contains an anti-inflammatory agent and/or an anti-bacterial agent. The sustained release system may be administered by intravitreal injection or implantation. In certain embodiments, the sustained-release system contains poly (D,L-lactide-co-glycolide) PLGA and dexamethasone. In other embodiments, the sustained-release system is an implant. The CAI may be provided a sonicated microparticle or in a molecular complex in formulation with hydroxypropyl β-cyclodextrin. The sonicated CAI microparticle or molecular complex may have a diameter of less than 10 micrometers. In certain embodiments, CAI is in a molecular complex formulation with 1 to 60 wt % hydroxypropyl β-cyclodextrin and one or more of glutamate, L-phenylalanine, a cellulose derivative (e.g. hydroxypropyl methyl cellulose), and a surfactant. In one embodiment, the sustained release system may be a non-erodible intravitreal implant. The sustained-release system may include an OZURDEX® (dexamethasone) intravitreal implant or an ILUVIEN® (fluocinolone acetonide) intravitreal implant.

The invention encompasses the use of any of the CAI compounds and formulations thereof in the manufacture of a medicament for the local treatment of a non-life threatening disease. In one embodiment, the invention encompasses the use of a CAI compound and a formulation, and preferably an aqueous formulation, thereof in the manufacture of a medicament for the local treatment of an ocular disease.

Other features and advantages of the invention will be apparent from the detailed description and examples that follow.

DETAILED DESCRIPTION OF THE INVENTION

Uveitis is inflammation or swelling of the uvea—the middle layer of the eye that consists of the iris, ciliary body and choroid. "Because the disease involves recurrent intraocular inflammation, uveitis can cause transient or permanent visual impairment and ocular complication that are not responsive to therapy." Barisani-Asenbauer et al., *Orphanet Journal of Rare Diseases* 2012, 7:57, the disclosure of which is incorporated as it pertains to uveitis. There are different types of uveitis based on where the inflammation occurs in the uvea:

Anterior uveitis is inflammation of the iris (iritis) or the iris and ciliary body;
Intermediate uveitis is inflammation of the ciliary body;
Posterior uveitis is inflammation of the choroid; and
Diffuse uveitis (also called panuveitis) is inflammation of all areas of the uvea.

The cause of uveitis is often unknown and frequently occurs in otherwise healthy people. However, it can also be associated with another illness such as an autoimmune disorder or an infection from a virus or bacteria. According to Barisani-Asenbauer et al. almost 20% of all uveitis cases involve infectious agents with ocular toxoplasmosis account for 7% of all cases and herpetic uveitis accounting for 7.1% of all cases. Barisani-Asenbauer et al. at pg. 5. In particular, causes of posterior uveitis include, but are not limited to, syphilis, toxoplasmosis, tuberculosis, endogenous endophthalmitis, and viral causes (including herpes simplex virus, herpes zoster virus, and cytomegalovirus). "In posterior uveitis cases 29% were caused by ocular toxoplasmosis and 17.7% by multifocal choroiditis." Barisani-Asenbauer et al. at Abstract. Common systemic infectious causes of uveitis include but are not limited to *Mycobacterium tuberculosis, Ascaris lumbricoides, Candida albicans, Chlamydia trachomatis*, Filaria, *Aspergillus fumigatus, Treponema pallidum, Giarda lamblia, Borrelia Burgdorferi*, and *Plasmodium falciparum*. Barisani-Asenbauer et al. Exemplary parasitic agents which cause uveitis include but are not limited to Toxoplasma, *Toxocara* (*Oxyuris* or ascariasis), and larva parasites. BenEzra et al., *Br J Ophthalmol.*, 2005; 89(4): 444-448, the disclosure of which is incorporated as it pertains to uveitis. A variety of symptoms may occur as a result of suffering from uveitis including blurred vision, floaters (dark floating spots in the field of vision), and eye pain. There are currently various treatments of uveitis. Most commonly, most types of uveitis including posterior uveitis are treated by the administration of steroids either orally or as eye drops. However, for infectious posterior uveitis, treatment with steroids does not address the underlying cause of the infection—the parasite. As such, there exists a need for a treatment for uveitis in particular infectious uveitis that not only relies on common steroid treatment but also eliminates the underlying cause of the inflammation.

According to the Merck Manual, toxoplasmosis (infection with *Toxoplasma gondii*) is one of the most common causes of retinitis (including posterior infectious uveitis) in immunocompetent patients. For posterior infectious uveitis caused by toxoplasmosis, the symptoms of floaters and decreased vision may be due to cells in the vitreous humor or to retinal lesions or scars. Current treatments involve multidrug therapy including pyrimethamine, sulfonamides, clindamycin, and, in select cases, systemic corticosteroids. See Merck Manual, Uveitis and related disorders.

The subject invention provides CAI compounds and formulations thereof, and methods for their use in the localized treatment of non-life threatening diseases. Formulations of CAI compounds of the subject invention can comprise CAI as a free base and a CAI prodrug in microcrystalline form, as a microparticle, as an emulsion, and the like. The subject invention further provides methods for treating non-life threatening diseases comprising administration to a patient of a therapeutically effective amount of a CAI compound of the invention (i.e., using novel delivery systems and combination therapies), that are effective and are associated with little or no adverse side effects.

In one embodiment, the invention provides for CAI compounds in time-release formulations, which may utilize CAI's anti-parasitic and/or anti-proliferative properties. In particular, the invention provides for CAI compounds in a time-release formulation to treat uveitis especially posterior infectious uveitis. When the CAI compound of the claimed invention are used in such a time-release formulation, the time-release formulation may include other therapeutic compounds such as an anti-inflammatory agent, an antibacterial agent or a glucorticoid. Thus, the invention provides for the use of CAI compound in combination therapy for the treatment of uveitis especially posterior infectious uveitis. Moreover, the invention provides for methods of reducing the inflammation in the eye due to the presence of a parasite (such as e.g. *Toxoplasma gondii*) by administering CAI compound in a time-release formulation.

Routes of administration contemplated herein for the delivery of CAI compounds and/or of formulations thereof by local administration include, but are not limited to, ocular, dermal, nasal, ictic, pulmonary, intravitreal, peribulbar, subtenon, periocular, retrobulbar, subretinal, and posterior juxtascleral subconjunctival routes. Such routes of administration may be performed by injection by syringe and using a needle or cannula or by needle-free systems: topical administration via a formulation comprising drops, ointment, and creams, inhalation by means of an inhalation device such as a metered dose inhaler or dry powder inhaler or nebulizer, or in conjunction with drug delivery systems exemplified by controlled release of a CAI compound from a matrix comprising a contact lenses (for delivery of drug to a tissue of the eye), from a device, from an implant, for release of drug to proximal tissue, and by use of an iontophoretic system e.g., to enhance the rate of penetration of drug through a barrier tissue.

In an embodiment of this invention, a CAI compound, or formulation thereof, is administered locally to ocular tissue via a route that attenuates ocular pathological disease processes without unduly compromising normal or healthy ocular function by acting directly in the eye (e.g., at the site of diseased tissue) in a controlled therapeutically effective and localized fashion.

In particular embodiments, the invention provides for using CAI compounds (such as e.g. 5-amino-[4-(4-chlorobenzoyl)-3,5-dichlorobenzyl]-1,2,3-triazole-4-carboxamide)) in the treatment of uveitis (including posterior infectious uveitis). The CAI compounds may be used alone or in combination with other components. In certain embodiments, the invention provides for the treatment of uveitis (in particular posterior infectious uveitis) using a sustained-release system (i.e. a time-release system). This time-release system may be a polymeric implant containing the CAI compound and additional agents. In certain embodiments, the polymeric implant also includes a glucocorticoid such as e.g. dexamethasone. In one embodiment, the sustained-release system may be an OZURDEX® (dexamethasone) intravitreal implant containing the CAI compound (e.g. 5-amino-[4-(4-chlorobenzoyl)-3,5-dichlorobenzyl]-1,2,3-triazole-4-carboxamide)).

I. DEFINITION OF TERMS

The term "CAI compound," as used herein, refers to CAI as a free base and to CAI analogs, and CAI prodrugs, and to any salts such as acid salts thereof. CAI (carboxy-amidotriazole) has the following structure:

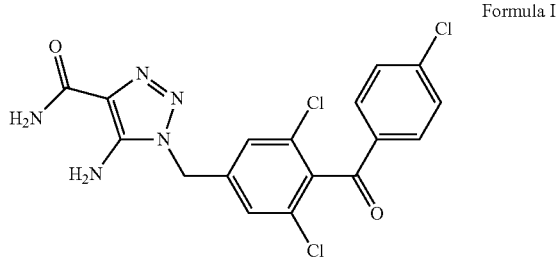 [SMILES: NC(=O)c1nnn(Cc2cc(Cl)c(C(=O)c3ccc(Cl)cc3)c(Cl)c2)c1N]

Formula I

The CAI compounds of the invention are particularly useful in the treatment of non-life threatening diseases.

The term "therapeutically effective amount," as used herein, refers to the amount necessary to elicit the desired biological response such as amelioration or reduction in severity of a symptom by a percentage amount. In accordance with the subject invention, the therapeutically effective amount of a CAI compound is the amount necessary to treat non-life threatening diseases. In one embodiment, an effective amount of a CAI compound, or formulation thereof, may ameliorate the severity of symptoms and/or complications associated with a non-life threatening disease. The amelioration in symptom and/or complication severity may be a 5%, 10%, 15%, 20%, 25% 30%, 35%, 40%, 45%, 50%, 55%, 60%, 65%, 70%, 75%, 80%, 85%, 90%, 95%, 98% or 99% decrease in severity. Preferably, the therapeutically effective amount of CAI compound locally administered in the treatment of ocular disease is a dose of 5 mg to 50 mg. More preferably, 5 mg is dosed intravitreally and 50 mg is dosed periocularly. More preferably, the CAI compound is CAI free base.

The term "patient," as used herein, describes an organism, including mammals, to which treatment with the compositions according to the present invention is provided. Mammalian species that benefit from the disclosed compounds and methods of treatment include, but are not limited to, apes, chimpanzees, orangutans, humans, monkeys; and domesticated animals (i.e., pets) such as horses, dogs, cats, mice, rats, guinea pigs, and hamsters.

The term "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "treatment" as used herein covers any treatment of a non-life threatening disease in a patient, particularly a human, comprising administration of a compound and/or formulation of a compound of this invention and methods of the subject invention, and includes:
1. Preventing the disease from occurring in a patient that may be predisposed to the disease but has not yet been diagnosed as having it;
2. Inhibiting the disease, e.g., inhibiting occurrence of an additional disease; or arresting development, inducing remission, or maintaining remission of the disease;
3. Relieving the disease, e.g., causing regression of the disease or addressing by diminishing or reducing symptoms; or
4. Inhibiting recurrence of a disease.

"Concurrent administration" and "concurrently administering," as used herein, includes administering a compound or formulation in a therapeutic method suitable for use with the compounds and methods of the invention (for example, administration of a CAI prodrug of Formulae II or III, below) in the treatment of serious, non-life threatening diseases.

"Non-life threatening disease(s)," as used herein, includes but is not limited to non-life threatening proliferative, inflammatory, neovascular, ocular, edematous, signal transduction-mediated diseases, matrix metalloproteinase-mediated diseases, and neurodegenerative diseases. Examples of serious, non-life threatening ocular diseases include, but are not limited to diabetic retinopathy (DR), neovascular age-related macular degeneration (ARMD), diabetic macular edema (DME), cystoid macular edema (CME) and ocular tumors such as retinoblastoma (RB), Retinopathy of Prematurity (ROP), Retinal Vascular Occlusions (RVO), corneal neovascularization, iris neovascularization, neovascular glaucoma, ischemic neural damage, uveitis (including, anterior uveitis, intermediate uveitis, posterior uveitis, posterior infectious uveitis, and diffuse uveitis), glaucoma, and pterygium, neovascular diseases of the retina such as hyperproliferative retinopathies, vitreoretinopathies, and retinal degeneration associated with systemic diseases such as diabetes mellitus, ischemic and hypoxic conditions associated with retinal vein and artery occlusion (e.g., from sickle cell disease or thrombosis), retinal degeneration resulting from retinal detachment, and age-related macular degeneration. Non-life threatening diseases, as defined herein, include any disease that is directly or indirectly mediated by CAI. Non-life threatening diseases are not diseases that may cause death in a patient. A non-life threatening disease may be present in a patient together with a life-threatening disease such as diabetes mellitus. In particular embodiments, the non-life threatening disease is uveitis or even more preferably posterior infectious uveitis.

The present invention may also be used to treat ocular symptoms resulting from diseases or conditions that have both ocular and non-ocular symptoms. Some examples include AIDS-related disorders such as cytomegalovirus retinitis and disorders of the vitreous; von Hippel-Lindau Syndrome (a disease that has ocular and nonocular neovascularizations); pregnancy-related disorders such as hypertensive changes in the retina; and ocular effects of various infectious diseases such as tuberculosis, syphilis, lyme disease, parasitic disease, *toxocara canis*, ophthalmonyiasis, cyst cercosis, and fungal infections. Examples of non-ocular diseases include but are not limited to rheumatoid arthritis, psoriasis, contact dermatitis, keratitis, conjunctivitis, scleritis, squamous cell carcinoma, condyloma, eczema, rosacea, vascular proliferation associated with angioplasty, graft vs host disease (organ and tissue transplantation), glioblastoma, peripheral neuropathies, diabetic neuropathy, collagen vasculidities.

In addition, the present invention can be used to treat diseases other than non-life threatening diseases such as, but not limited to, bladder cancer, breast cancer, brain tumors, colon and rectal cancer, endometrial cancer, kidney cancer, leukemia, lung cancer, melanoma, non-Hodgkin's lymphoma, pancreatic cancer, prostate cancer, skin (non-melanoma) cancer, and thyroid cancer.

The following definitions are applicable to those structures as defined for Formula II and Formula III, below.

Unless otherwise specified, as used herein, the term "alkyl" refers to a straight or branched chain alkyl moiety. In one embodiment, the alkyl moiety is $C_{1-8}$ alkyl, which refers to an alkyl moiety having from one to eight carbon atoms, including for example, methyl, ethyl, propyl, isopropyl, butyl, tert-butyl, pentyl, hexyl, and octyl.

The term "alkyl" also includes cycloalkyl, including for example cyclohexyl and the like. The term "alkyl" also includes alkenyl, which refers to a straight or branched alkyl moiety having one or more carbon double bonds, of either E or Z stereochemistry where applicable, and includes for example, vinyl, 1-propenyl, 1- and 2-butenyl, and 2-methyl-2-propenyl.

The term "alkyl" also refers to an alicyclic moiety having from three to six carbon atoms and having in addition one double bond. Such groups, also known as "cycloalkenyl," include, for example, cyclopentenyl and cyclohexenyl.

The term "alkyl" also includes alkynyl moieties, including for example, ethynyl, 1-propynyl, 1- and 2-butynyl, 1-methyl-2-butynyl, and the like.

The term "alkoxy" refers to an alkyl-O-group, in which the alkyl group is as described herein.

The term "halogen" is refers to fluorine, chlorine, bromine and iodine.

The term "aryl" refers to an aromatic carbocyclic ring, e.g., phenyl, substituted phenyl, and like groups, as well as rings, which are fused, e.g., naphthyl, biphenyl indaryl and the like. Aryl groups may be optionally substituted with from 1 to 3 groups of alkyl, aryl, heteroaryl, halogen, hydroxy, alkoxy, nitro, cyano, trifluoromethyl, alkylthio, alkylsulfonyl, arylsulfonyl, $N(R)_2$, $S(O)_2N(R)_2$, $CH_2N(R)_2$, $CO_2R$, and $C(O)N(R)_2$ wherein R groups are independently hydrogen, alkyl, alkoxyalkyl, hydroxyalkyl, aminoalkyl, arylalkyl, aryl, heterocycloalkyl or heteroaryl.

The term "arylalkyl" refers to a moiety in which the "aryl" and "alkyl" groups are as described herein.

The term "heterocycloalkyl" refers to a saturated heterocyclic moiety having from two to six carbon atoms and one or more heteroatom from the group N, O, and S (or oxidized versions thereof) which may be optionally benzofused at any available position. This includes, for example, azetidinyl, pyrrolidinyl, tetrahydrofuranyl, piperidinyl, benzodioxolyl and the like.

The term "heterocycloalkyl" also refers to an alicyclic moiety having from three to six carbon atoms and one or more heteroatoms from the group N, O, and S and having in addition one double bond. Such moieties may also be referred to as "heterocycloalkenyl" and includes, for example, dihydropyranyl, and the like.

In the case that the heterocyclyl moiety contains a nitrogen atom that may be substituted, then a substituent may be chosen from the group of R.

The term "heteroaryl" refers to monocyclic or bicyclic aromatic ring systems of five to ten atoms of which at least one atom is selected from O, N, and S, in which a carbon or nitrogen atom is the point of attachment, and in which one additional carbon atom is optionally replaced with a heteroatom selected from O or S, and in which from 1 to 3 additional carbon atoms are replaced by nitrogen heteroatoms. The heteroaryl group is optionally substituted with up to three groups selected from alkyl, aryl, heteroaryl, halogen, hydroxy, alkoxy, nitro, cyano, trifluoromethyl, alkylthio, alkyl sulfonyl, aryl sulfonyl, $N(R)_2$, $S(O_2)N(R)_2$, $CH_2N(R)_2$, $CO_2R$, and $C(O)N(R)_2$ wherein R groups are independently hydrogen, alkyl, alkoxyalkyl, hydroxyalkyl, aminoalkyl, arylalkyl, aryl, heterocycloalkyl or heteroaryl. This term includes, for example, imidazolyl, tetrazolyl, furanyl, thiophenyl, pyridyl, indolyl, quinolyl, benzothiadiazolyl, benzofurazanyl, benzotriazolyl, and the like.

Certain of the above-defined terms may occur more than once in Formulas II and III and upon such occurrence each term shall be defined independently of the other.

"Optional" or "optionally" means that the subsequently described event, element, or circumstance may or may not occur, and that the description includes instances where said event occurs and instances in which it does not.

The term "substituted" shall be deemed to include multiple degrees of substitution by a named substituent.

Where multiple substituent moieties are disclosed, the substituted compound can be independently substituted by one or more of the disclosed or claimed substituent moieties, singly or plurally.

II. CAI PRODRUGS OF THE INVENTION

In certain embodiments of the subject invention, CAI prodrugs of Formula II are provided as follows:

Formula II

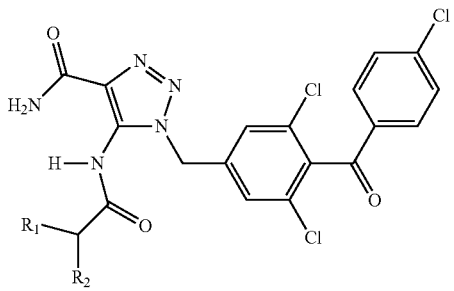

wherein
R₁ is selected from hydrogen, alkyl, aryl, arylalkyl, alkylamino, dialkylamino, morpholino, piperazinyl, alkylpiperazinyl, hydroxy, alkoxy, hydroxyalkyl, and alkoxyalkyl or is a group of formula

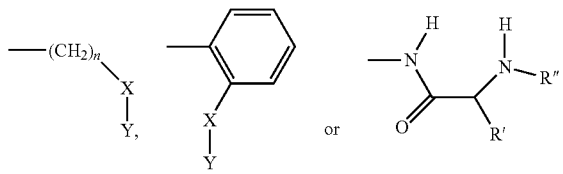

wherein X is O, NH or S; Y is selected from hydrogen, alkyl, alkylamino, dialkylamino, and hydroxyalkyl; R' is selected from hydrogen and a naturally occurring α-amino acid side chain; R" is selected from hydrogen, alkyl, alkylamino, and alkylhydroxy.

R₂ is selected is selected from hydrogen, alkyl, aryl, arylalkyl, alkylamino, dialkylamino, morpholino, piperazinyl, alkylpiperazinyl, hydroxy, alkoxy, hydroxyalkyl, alkoxyalkyl, alternatively when taken together may form a carbocyclic, heterocyclic and heteroaryl ring In certain other embodiments of the subject invention, CAI prodrugs of Formula III are provided as follows:

Formula III

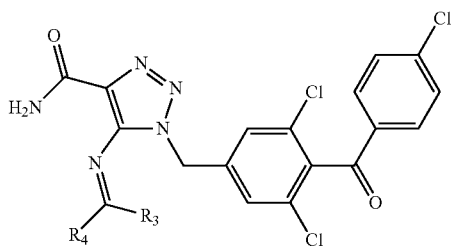

wherein
R₃ is selected from hydrogen, alkyl, aryl, alkylaryl and heteroaryl or is a group of formula

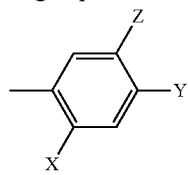

wherein X, Y and Z are independently hydrogen, hydroxy, alkoxy, amino, alkylamino, dialkylamino, halogen, nitro or cyano.

R₄ is hydrogen, alkyl, aryl, alkylaryl or heteroaryl, or a group of formula

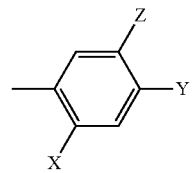

wherein X, Y and Z are independently hydrogen, hydroxy, alkoxy, amino, alkylamino, dialkylamino, halogen, nitro or cyano.

Suitable embodiments of CAI prodrugs of Formula II are those that provide for a high therapeutic margin of safety via conversion to CAI at a rate that yields localized therapeutic effects in target tissues (such as ocular tissues, where esterase conversion of an esterified prodrug of CAI is an embodiment) and compartment of administration. The preferred prodrug compounds of the subject invention are particularly advantageous because they provide an acceptable safety profile consistent with acute and/or chronic ocular disease.

In one embodiment, CAI prodrugs can readily penetrate the human scleral tissue and effectively deliver the biologically active parent CAI therapeutic entity to the ocular disease target tissue compartment(s) in therapeutic concentration without causing ocular toxicity that has been previously described for the CAI parent drug when administered systemically to cancer patients. CAI prodrugs of the present invention may be converted to CAI parent drug, after administration, by both passive (e.g. by pH dependent aqueous hydrolysis) or biologically mediated (e.g. enzymatic) mechanisms.

In certain embodiments, CAI prodrugs of the invention can be converted in vivo into biologically active CAI with passive hydrolytic mechanisms. For example, a CAI prodrug of Formula II can be converted to CAI in vivo by spontaneous hydrolysis. The rate of spontaneous hydrolysis of CAI prodrugs of Formula II may be tuned by appropriate choice of the R₁ and R₂ groups. Specifically, to favor the spontaneous hydrolysis of compounds of Formula II, one embodiment provides for compounds of Formula II that contain nucleophilic catalytic groups, such as amino and hydroxyl functions, incorporated into either or both of the R₁ and R₂ groups such that internal "anchimeric assistance" of the hydrolytic reaction is catalyzed via formation of a cyclic intermediate with a ring size ranging from 3-7 atoms.

Alternatively, endogenous hydrolytic enzymes such as proteases and esterases in the eye may mediate the conversion of CAI amide prodrugs of Formula II to CAI in vivo. Such hydrolytic enzymes particularly matrix metalloproteinase are known to be upregulated in target neovascular disease tissues for the neovascular proliferative disease indications of relevance specified herein. CAI amide prodrugs of Formula II may contain one or more asymmetric carbon atoms and may exist in a given diastereomeric, racemic, or enantiomeric form.

Imine and amide derivatives of amino functions and are well established prodrugs in the medicinal chemistry art. As described above, CAI is a known organic compound designated as 5-amino-[4-(4-chlorobenzoyl)-3,5-dichlorobenzyl]-1,2,3-triazole-4-carboxamide and having a structure illustrated in Formula I. The amorphous CAI free base, which is the starting material for crystalline forms, salt forms, and other formulations that are the subject of this invention, is readily synthesized using previously described methods (see, for example, U.S. Pat. Nos. 4,590,201 and 5,602,156, the contents of which are hereby incorporated by reference in their entirety) by a person who is skilled in the art of organic synthesis. CAI amide prodrugs of Formula II are readily synthesized by persons skilled in the art for example by reacting CAI with a reactive carboxylic acid derivative (e.g. carboxylic acid chloride or anhydride) in the presence of a base such as an organic base in an organic solvent to promote amide bond formation. Examples of carboxylic acid chlorides and anhydrides include but are not limited to acetyl chloride, benzoylchloride, propionic anhydride, pivaloyl chloride; examples of organic bases include pyridine, 4-dimethylaminopyridine and triethylamine and appropriate organic solvents include dimethylformamide, tetrahydrofuran and dichloromethane. Compounds of Formula III are readily synthesized by persons skilled in the art by reacting CAI with the specific ketone or aldehyde compound in an organic solvent in the presence of a catalyst or drying agent to form the CAI ketamine or aldimine prodrugs. Examples of ketones and aldehydes include but are not limited to acetaldehyde, proprionaldehyde, benzaldehyde, acetophenone, benzophenone, acetone and ethylmethylketone; organic solvents include dimethylformamide, tetrahydrofuran and dichloromethane; catalysts and drying agents are exemplified by magnesium sulfate and titanium tetraisopropoxide.

III. CAI SALTS OF THE INVENTION

Further embodiments of the present invention are novel acid addition salt forms of CAI free base and CAI prodrugs that are used to prepare a pharmaceutical formulation using any of the formulation techniques known to the skilled artisan or as set forth herein. Particularly preferred are acid addition salt forms that, upon local administration, serve to maintain a therapeutic, free concentration of CAI that is effective at alleviating disease pathology and have a safety profile consistent with practical therapeutic application.

Certain embodiments of the subject invention provide acid addition salt forms of CAI derived from organic acids that have membrane stabilizing or anti-inflammatory effects including, but not limited to, cholic acids, long chain unsaturated fatty acids, and amphilic long chain and sterol derived sulfonic acids. Such salts and complexes may be prepared in a conventional manner and can exhibit superior activity, and controlled release profile in vivo relative to the simple CAI parent free base. Such salts refer to non-toxic or biocompatible salts of CAI or CAI prodrugs of the invention that are generally prepared by one skilled in the art by reacting the CAI in its free base parent form with a suitable organic or inorganic acid.

Representative organic or inorganic acids for the preparation of CAI and CAI prodrug salts of the subject invention include, but are not limited to, the following: hydrogen borate, hydrogen bromide, hydrogen chloride, nitric acid and hydrogen nitrate, phosphoric acid or trihydrogen or dihydrogen or monohydrogen phosphate, dihydrogenphosphate, sulfuric acid or dihydrogen sulfate, and monohydrogensulfate. Representative hydrophilic organic acid salts include, but are not limited to, the following: citrate, fumarate, gluconate, glutamate, lactate, maleate, mandelate, mesylate, oxalate, succinate tartrate, and valerate. Representative hydrophobic organic acid salts include, but are not limited to, the following: benzenesulfonate, benzoate, cholate, hydroxynaphthoate, laurate, napsylate, oleate, palmoate, palmitate, salicylate, stearate, tosylate, and taurocholate. Additional salts of essential amino acids are useful.

Particularly preferred are acid addition salt forms of CAI that, upon local administration, serve to maintain a therapeutic concentration of free form CAI that is effective at alleviating disease pathology without a toxic or tissue-damaging or tissue function-impairing side effect profile that can prohibit practical therapeutic use. Even more preferred embodiments are acid addition salt forms of CAI derived from or comprising organic acids that have membrane stabilizing or anti-inflammatory effects such as cholic acids, long chain unsaturated fatty acids, and amphilic long chain and sterol derived sulfonic acids.

IV. CAI COMPOUND FORMULATIONS

In a further embodiment, formulations of CAI compounds are provided for treatment of the non-life threatening diseases, which formulations and methods of treatment comprise the subject of this invention. Such formulations serve to overcome bioavailability limitations of CAI as a poorly water-soluble compound and/or provide for the increased, with respect to an aqueous solution of free base CAI, bioavailability of free CAI drug to the targeted disease tissue and providing exposure to diseased tissue at a desired rate to achieve and maintain a therapeutically effective amount of CAI in a pharmacologically active concentration.

In one embodiment, aqueous CAI compound formulations administered as described herein provide for immediate and complete release of CAI from a formulation. Alternatively, aqueous CAI compound formulations of the invention, when administered, provide for a slow rate of CAI release such as a controlled release or a zero order release or release of about 1% to 5% of the amount of administered drug over a time period of from about 1 hour to about 1 month. In related embodiments, formulations of CAI compounds of the invention include, but are not limited to, microcrystalline forms, micron and submicron solid particulate formulations, emulsion and microemulsion formulations and polymer encapsulation formulations where the drug can be dissolved or suspended in a matrix comprising a biocompatible and/or biodegradable polymer.

Accordingly, in one embodiment, 5-amino-[4-(4-chlorobenzoyl)-3,5-dichlorobenzyl]-1,2,3-triazole-4-carboxamide is dissolved, suspended, encapsulated or otherwise incorporated in a polymeric matrix to create a sustained-release system. The polymeric matrix may be a polylactic-coglycolic acid such as e.g. poly (D,L-lactide-co-glycolide) PLGA. In one embodiment, the matrix may be the NOVADUR® solid polymer sustained-release drug delivery system. The system and/or matrix may be free of a preservative. The system may also contain other components described below.

In another embodiment, the CAI compound formulations of the invention provide a slow rate of CAI release in the target disease tissue over a 1-week to 3-year period after a single administration. Certain CAI compound formulations of the invention provide pharmacologically effective concentrations of CAI in the target disease tissue over a 15 minute to one-week period week after single administration.

The CAI compound formulations described below can be prepared in proportions of ingredients (CAI compound and pharmaceutically acceptable ingredients such as excipients, surface-active agents, solvents, and the like) of which are determined by the solubility and chemical nature of the CAI compound or formulation, chosen route of administration, and standard medical practice. For example, microparticle formulations of CAI can be further prepared in an aqueous formulation, for example in the presence of a pharmaceutically acceptable surfactant or a pharmaceutically acceptable surface-active agent.

A. Emulsion Formulations

Emulsion formulations of CAI compounds of the invention include, but are not limited to, compositions prepared using formulation processes comprising a lipid, surfactant, and solvent that are readily performed by one skilled in the art of drug formulation. In a one embodiment emulsion formulations of CAI compounds to be administered as described herein, provide for immediate or short term release of at least 90% of the amount of CAI in the formulation and providing pharmacologically effective concentrations of CAI in the target disease tissue over a 15 minute to one-week period week after single administration.

In general emulsion formulations of CAI compounds of the invention are prepared using a selection of the following five classes of excipients (Pouton, C. W. Eur. J. Pharm. Sci. 11 Suppl 2: S93-98, 2000): 1) pure triglyceride oils; 2) mixed glycerides; 3) lipophilic surfactants; 4) hydrophilic surfactants; and 5) water-soluble cosolvents. Examples of lipid based drug formulations applicable to CAI, CAI prodrug and salts thereof include emulsions prepared for the lipophilic immunosuppressive drug cyclosporine (Fahr, A. et al. Clin. Pharmacokinet. 24, 472-495, 1993; Fricker, G. et al. Br. J. Pharmacol. 117, 217-223, 1996), and halofantrine a lipophilic small molecule antimalaria drug (Porter, C. J., et al. J. Pharm. Sci. 85, 357-361, 1996).

In certain embodiments, emulsion formulations of the invention comprising liquid droplets of formulation comprising CAI or a CAI compound, which droplets are surface stabilized dispersions of droplets of sizes less than 10 micrometers in aqueous medium. Alternatively, the subject invention's emulsion formulations can be locally delivered to a target tissue as an oil-in-water microemulsion of droplet sizes less than 100 nanometers. These microemulsions are composed of CAI, CAI prodrugs and salts thereof dissolved in a mixture of lipophilic vehicle and admixed with surfactants and cosurfactants.

In other embodiments, both these end results (lipophilic carrier and admixture with surfactants and cosurfactants) are achieved from a preconcentrated or a concentrated solution of a CAI compound in a vehicle that forms oil-in-water emulsion of droplet sizes less than 10 micrometers spontaneously upon mixing with bodily fluids (i.e., lacrimal fluid, vitreal fluid, scleral fluid, blood, cerebral spinal fluid, vaginal fluid, mucous). Alternatively, emulsion formulations of the invention can be achieved from a preconcentrated or a concentrated solution of a CAI compound in a vehicle that forms oil-in-water microemulsion of droplet sizes less than 100 nanometers spontaneously upon mixing with bodily fluids. In this way, in-situ generation of the small size droplets is facilitated wherein application of energy is not required.

Emulsion formulations of CAI compounds are generally selected and prepared as described below. First, suitable pharmaceutically acceptable oil or triglyceride vehicles preferably a readily available pharmaceutically acceptable oil or pharmaceutically acceptable triglyceride vehicle (such as pure triglyceride oils) is selected from a commercial source e.g. soybean oil (Fluka, Buchs, Switzerland), sesame oil (Fluka, Buchs, Switzerland), Miglyol® (810, 812, 818, Hulls, Puteaux, France) and other candidates selection of which is preferably based on respectively highest solubility and longest term of stability of the pure CAI, CAI salts or prodrugs as active ingredient in the oil, solubility and stability determined in preformulation evaluation by dissolving CAI in the vehicle, +/−surfactant, +/−water (optionally containing a buffer salt) to determine saturation concentrations of CAI as a function of temperature and then determining the stability of CAI as a function of time (1 day, 2 days, 4 days, 1 week 2 weeks, 4 weeks, 1 month, 2 months, and monthly thereafter, each at constant temperatures of about 20° C., 30° C., and 40° C. Formulations containing hydrophobic surfactants and hydrophilic surfactants are then prepared with an oil vehicle composition range of 25-45%, hydrophobic surfactant(s) range of 25-45% and hydrophilic co-surfactant(s) in a range of 10-20%.

Contemplated hydrophobic surfactants for use in the preparation of emulsion formulations of the invention include, but are not limited to, glyceryl monostearate and Pluronic® (e.g., Pluronic®F68, Pluronic®F127, Sigma, St. Louis Mo.). Contemplated hydrophilic co-surfactants include but are not limited to, Tween® (e.g., Tween® 20, Tween® 40, Tween® 80, Sigma, St. Louis Mo.) and Labrasol® (Gattefosse, Saint Priest, France). Preferred emulsion formulations of the invention exhibit small submicron droplet size, high CAI active ingredient stability, and high CAI active ingredient load.

Alternatively, in accordance with the subject invention, a CAI compound can be formulated as an aqueous suspension of surface stabilized particles. The particle size distribution of such suspension formulations is carefully maintained to less than 10 micrometers so that local irritation to the target tissue (for example, tissue of the eye) is avoided. For example, one embodiment of the invention provides a preparation of concentrated solution of a CAI compound. Specifically, the CAI compound is dissolved or suspended directly in vehicles that form a suspension of surface stabilized CAI compound with particles of sizes less than 10 micrometers. The vehicles provide therapeutically effective concentrations of pharmacologically active CAI at the target disease site upon local administration to the disease target tissue or tissue compartment by administration methods described herein. Surface stabilization of the particles in these embodiments is provided by a pharmaceutically acceptable surface active agent, for example a surface active agent selected from the group consisting of lecithin, charged or uncharged phospholipids, polymeric surfactants, non-polymeric surfactants, charged surfactants (e.g., anionic surfactants or cationic surfactants), uncharged surfactants (e.g., polyether surfactants such as polyethyleneglycol-containing surfactants and polyethyleneglycol-co-polypropyleneglycol-containing surfactants), one or more of bile acids and their salts, or combinations thereof.

B. Beta-Cyclodextrin Complexes

Alternatively, the CAI compounds of the invention, such as e.g. CIA, can be prepared as a molecular complex with beta-cyclodextrin or its derivatives. Furthermore, an alternative formulation consists of molecular complex of a CAI compound with one or more pharmaceutically acceptable lipids selected from a group of lecithin, charged or uncharged phospholipids, polymeric surfactants, non-polymeric surfactants, charged surfactants, uncharged surfactants, one or more of bile acids and their salts, triglycerides, or other lipophilic solvents or combinations thereof.

Thus, in certain embodiments, CAI may be in a molecular complex formulation with 1 to 60 wt % hydroxypropyl β-cyclodextrin in formulation, wherein the formulation further contains at least a cellulose derivative, and a surfactant. In other embodiments, the formulation contains glutamate and/or L-phenylalanine. The cellulose derivate may be hydroxypropyl methyl cellulose. These complexes may have a diameter of less than about 10 micrometers.

C. Microparticle Formulations

"Microparticlulate forms of a CAI compound" refers to solid particulate forms of CAI free base, CAI prodrugs and salts thereof with particle sizes of 10 micrometers or less. Further, "microparticulate forms of a CAI compound" refers to respective amorphous or crystalline forms CAI, CAI prodrugs and salts thereof as well as mixtures of CAI, CAI prodrugs and salts thereof with other additives (e.g. polymers, surfactants) that yield particulate forms of 10 micrometers or less.

Microparticle formulations of CAI compounds of the invention include, but are not limited to, compositions prepared using controlled precipitation formulation processes readily selected and implemented by one skilled in the art of drug formulation. For example, by dissolving a CAI compound in a solvent such as acetone or ethanol or tetrahydrofuran or DMSO to form a solution and then adding said solution to a non-solvent such as water in which the solvent has solubility, or adding such non-solvent slowly with stirring to the solution, each method optionally in the presence of a pharmaceutically acceptable surface active agent or combination of agents in either the solvent or non-solvent or in both, followed by removal of the solvent, such as by evaporation or diafiltration to provide a suspension of microparticles in an aqueous medium. The particles can be isolated by lyophilization of the suspension, for example in vials optionally in the presence of an oxygen-free gas such as nitrogen or argon after removal of the water, optionally after addition of a carbohydrate such as lactose or mannitol which can form a solid matrix in which the solid particles are dispersed. The particles can be resuspended into an aqueous medium upon addition of such aqueous medium. In an embodiment, microparticulate formulations of a CAI compound to be administered as described herein, provide for immediate release of CAI providing pharmacologically effective concentrations of CAI in the target disease tissue over a one-week to three-year period after a single administration.

In one embodiment, microparticles of CAI of the invention include polymeric microspheres that encapsulate CAI, CAI prodrugs and salts thereof of the invention. Microparticle formulations of CAI include, but are not limited to, compositions prepared using controlled precipitation formulation processes readily selected and implemented by one skilled in the art of drug formulation. A controlled microparticle precipitation process is exemplified as follows.

CAI free base or a respective CAI acid addition salt form or prodrug is dissolved in a suitable organic solvent (e.g. ethanol, N-methylpyrrolidine) and then mixed with stabilizers, as exemplified by SPG (0.218 sucrose; buffer salts comprising 0.0038 M monobasic, 0.0072 M dibasic potassium phosphate; 0.0049 M potassium glutamate). Polymer (e.g. polyvinylpyrrolidone) and sugar (e.g. lactose) matrix-forming components are optionally added. Micron and submicron microparticles of CAI formulation are then prepared by controlled precipitation at an optimized temperature under low frequency sonication followed. Sonication of the contents of the vessel containing the components of such formulation can also be accomplished using ultrasound frequencies, for example by placing the vessel containing the formulation in an ultrasound bath and applying ultrasound energy. The CAI microparticle formulation(s) are collected, for example by centrifugation such as at 10,000 g and characterized by digital optical light microscopy and laser light scattering and Scanning Electron Microscopy (SEM) for particle sizing. Contents of the formulation are analyzed, for example by using HPLC for content and stability of such content, and by using USP dissolution techniques to measure the release rate of the CAI drug in vitro. Thus, in one embodiment, CAI is provided as a sonicated microparticle. In certain embodiments, especially when used to treat uveitis, the sonicated CAI microparticles may be of a size less than about 10 micrometers.

In yet another embodiment, the CAI microparticle formulation is prepared using methods that are standard in the art, such as by entrapment or encapsulation of CAI free base, CAI salt form or prodrug drug molecules within a matrix of polymeric microspheres of sizes less than 50 micrometers, wherein the polymeric matrix material is selected from the group of albumin, polylactic-coglycolic acid, polymethacrylic acids and salts, polyethyleneglycol, natural polymeric materials, synthetic polymeric materials, charged polymeric materials, and uncharged polymeric materials, and combinations thereof.

Suitable polymer encapsulation systems include polylactic-coglycolic acid (PLGA) microsphere formulations as exemplified by the formulation of octreotide in Sandostatin-LAR® (See Sandostatin LAR® prescribing information) which is administered as a once-a-month depot injectable therapeutic.

D. Liposomal Formulations

In addition, the compounds of the present invention can also be administered in the form of liposomes or the like. Disintegrators include, without limitation, delivery systems such as small unilamellar vesicles, large unilamellar vesicles and multilamellar vesicles. Liposomes can be formed from a variety of phospholipids, such as lecithin and phosphatidylcholines, optionally with added cholesterol and/or stearylamine.

D. Pharmaceutical Formulations, in General

CAI compounds of the invention may be provided in formulations that contain pharmaceutically acceptable auxiliary substances as required to approximate physiological conditions, such as pH adjusting for example to adjust pH of an aqueous medium, for example to about pH 7.4 and buffering agents to maintain such pH, tonicity adjusting agents which can be useful, for example, to adjust tonicity of a formulation to physiological ionic strength, wetting agents and the like, for example, sodium acetate, sodium lactate, sodium chloride, potassium chloride, calcium chloride, sorbitan monolaurate, triethanolamine oleate, etc.

The concentration of the CAI compounds of the invention in their respective pharmaceutical formulations can vary widely (% w/v), i.e., from less than about 0.1%, usually at or at least about 2% to as much as 20% to 50% or more by weight, and will be selected primarily by desired dosage levels, fluid volumes, viscosities, etc., in accordance with the particular mode and route of administration selected and target tissue. Preferably, the concentration of CAI compound in the aqueous, therapeutic formulations of the invention range from about 0.01 mg/mL to about 100 mg/mL. More preferably, the concentration of CAI compound in the aqueous, therapeutic formulations of the invention for the localized treatment of ocular diseases range from about 1 mg/mL to 60 mg/mL of formulation.

The pharmaceutical formulations of the invention may include delivery-enhancing agents that can be used alone, in combination with each other, or in combination with another delivery-enhancing agent. The term "delivery enhancing agents" includes agents that facilitate the transfer CAI to the target cell. Examples of such delivery enhancing agents include, but are not limited to, fatty acid esters, surfactants, detergents, alcohols, glycols, surfactants, bile salts, heparin antagonists, cyclooxygenase inhibitors, hypertonic salt solutions, acetates.

As contemplated herein, alcohols that can act as delivery enhancing agents include, without limitation, the aliphatic alcohols such as ethanol, N-propanol, isopropanol, butyl alcohol, acetyl alcohol. Glycols that can act as delivery enhancing agents in accordance with the subject invention include, but are not limited to, glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents.

Examples of pharmaceutically acceptable surfactants that can be provided in pharmaceutical formulations of the invention include, without limitation, sodium dodecyl sulfate (SDS) and lysolecithin, polysorbate 80, nonylphenoxypolyoxyethylene, lysophosphatidylcholine, polyethyleneglycol 400, polysorbate 80, polyoxyethylene ethers, polyglycol ether surfactants and DMSO. Bile salts such as taurocholate, sodium taurodeoxycholate, deoxycholate, chenodesoxycholate, glycocholic acid, glycocheno-deoxycholic acid and other astringents like silver nitrate may be used. Heparin-antagonists like quaternary amines such as protamine sulfate may also be used. Cyclooxygenase inhibitors such as sodium salicylate, salicylic acid, and non-steroidal anti-inflammatory drug (NSAIDS) like indomethacin, naproxen, diclofenac may be used.

Examples of pharmaceutically acceptable detergents that can be provided in pharmaceutical formulations of the invention can be selected from anionic, cationic, zwitterionic, and nonionic detergents. Exemplary pharmaceutically acceptable detergents include but are not limited to taurocholate, deoxycholate, taurodeoxycholate, cetylpyridium, benalkonium chloride, ZWITTERGENT-3-14 detergent, CHAPS (3-{(3-Cholamidopropyl)dimethylammoniol}-1-propanesulfonate hydrate, Aldrich), Big CHAP, Deoxy Big CHAP, TRITON™ X-100 detergent, C12E8, Octyl-B-D-Glucopyranoside, PLURONIC® F68 detergent, TWEEN® 20 detergent, and TWEEN® 80 detergent.

The concentration of a delivery-enhancing agent in a pharmaceutical formulation of the invention will depend on a number of factors known to one of ordinary skill in the art. Such factors include the particular delivery-enhancing agent being used, the buffer, pH, target tissue or organ and mode of administration. In certain embodiments of the invention, the concentration of the delivery-enhancing agent will be in the range of 1% to 50% (v/v), preferably 10% to 40% (v/v), and most preferably 15% to 30% (v/v). Preferably, the detergent concentration in the final formulation administered to the patient is about 0.5 to about 2 times the critical micellization concentration (CMC).

Excipients can be included in the formulations of the invention. Examples include cosolvents, surfactants, oils, humectants, emollients, preservatives, stabilizers, and antioxidants. A pharmacologically acceptable buffer may be used, e.g., tris or phosphate buffers. Effective amounts of diluents, additives, and excipients are those amounts, which are effective to obtain a pharmaceutically acceptable formulation in terms of solubility, stability, and biological activity.

Formulations of the invention may also include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents that are especially useful for injectable formulations are water, the various commercially available pharmaceutically-acceptable saline, organic, or inorganic salt solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Carrier employed may be, for example, either a solid or liquid. Examples of solid carriers include lactose, terra alba, sucrose, talc, gelatin, agar, pectin, acacia, magnesium stearate, stearic acid, and the like. Examples of liquid carriers include syrup, peanut oil, olive oil, water, and the like. Similarly, a carrier for oral use may include time delay material well known in the art, such as glyceryl monostearate or glyceryl distearate alone or with a wax.

In certain embodiments, pharmaceutical formulations comprise a CAI compound (preferably, CAI itself) and a carrier such as inclusion compound host materials. The "inclusion compound host materials" as described herein, interact with the CAI compound to increase aqueous solubility, increase chemical stability, and/or enhance drug (such as CAI compound) delivery to and through biological membranes. It is believed that by providing a carrier such as inclusion compound host materials, a stabilized CAI compound molecule can be safely delivered to a patient at a dosage that will not induce toxicity. In addition, such carrier materials can include coating materials (i.e., enteric-coatings) that allow dissolution of the coating in an alkaline environment such as in the intestines.

Inclusion compound host materials that can be used in accordance with the subject invention include those disclosed in U.S. Published Patent Application No. 2004/0033985, incorporated herein by reference in its entirety. Contemplated inclusion compound host materials include proteins (such as albumin), crown ethers, polyoxyalkylenes, polysiloxanes, zeolites, cholestyramine, colestipol, colesevelam, colestimide, sevelamer, cellulose derivatives, dextran derivatives, starch, starch derivatives, and pharmaceutically acceptable salts thereof. Contemplated cellulose derivatives and dextran derivatives include DEAE-cellulose, guanidinoethylcellulose, or DEAE-Sephadex. Favorable starches or starch derivatives to be included in the compositions of the invention include cyclodextrin, retrograded starch, degraded starch, a combination of retrograded and degraded starch, hydrophobic starch, amylase, starch-diethylaminoethylether, and starch-2-hydroxyethyl ether.

According to the subject invention, aqueous CAI compound formulations comprise CAI and inclusion compound host materials selected from, but not limited to, cyclodextrin and/or its derivatives (i.e., methyl β-cyclodextrin (M-β-CD), hydroxypropyl β-cyclodextrin (HP-β-CD), hydroethyl β-cyclodextrin (HE-β-CD), polycyclodextrin, ethyl β-cyclodextrin (E-β-CD) and branched cyclodextrin). As one skilled in the art will appreciate, any cyclodextrin or mixture of cyclodextrins, cyclodextrin polymers, or modified cyclodextrins can be utilized pursuant to the present invention. Cyclodextrins are available from Wacker Biochem Inc., Adrian, Mich. or Cerestar USA, Hammond, Ind., as well as other vendors. Formation of inclusion complexes using cyclodextrin or its derivatives protects the constituent (i.e., CAI compound) from loss of evaporation, from attack by oxygen, acids, visible and ultraviolet light and from intra- and intermolecular reactions.

The general chemical formula of cyclodextrin is $(C_6O_5H_9)_n$. The content of inclusion compound host materials in compositions of the subject invention can range from about 1 to 80 wt %. Preferably, the content of inclusion compound host materials in compositions of the invention range from about 1 to 60 wt %. The actual amount of the inclusion compound host materials used will depend largely upon the actual content of CAI compound and therapeutic agents, if any, used in preparing compositions of the invention.

Preferably, aqueous pharmaceutical formulations of CAI compounds can be prepared as molecular complexes with beta-cyclodextrin or its derivatives. Furthermore, an alternative pharmaceutical formulation consists of molecular complex of CAI compound(s) with one or more lipids selected from a group of lecithin, charged or uncharged phospholipids, polymeric surfactants, non-polymeric surfactants, charged surfactants, uncharged surfactants, one or more of bile acids and their salts, triglycerides, or other lipophilic solvents or combinations thereof.

The CAI compound and aqueous formulations thereof of the subject invention can be formulated according to known methods for preparing pharmaceutically useful compositions. Formulations are described in a number of sources, which are well known and readily available to those skilled in the art. For example, *Remington's Pharmaceutical Science* (Martin E W [1995] Easton Pa., Mack Publishing Company, $19^{th}$ ed.) describes formulations that can be used in connection with the subject invention. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Certain embodiments of the invention may be formulated for local instillation in or around tissue or organs, where for specific targeted local therapy for non-ocular body sites, parenteral therapy is used to achieve safe and effective local drug concentrations into a defined target lesion or disease area, or tissue(s), or organ(s), or body compartment(s), wherein routes of administration of formulations of CAI compounds can include transcutaneous, subcutaneous, intradermal, intrathecal, intracerebellar, intramuscular, intra-articular or intravenous, when such direct application is practical and clinically indicated.

Alternatively, certain embodiments of the invention may be formulated for systemic administration to a patient diagnosed with a non-life threatening disease.

The CAI compounds of the invention can be administered in topical formulations or polymer matrices, hydrogel matrices, polymer implants, or encapsulated formulations to allow slow or sustained-release of the compositions. A particularly suitable formulation is a suspension or solution of the delivery system in a topical ocular formulation, such as eye drops.

Topical applications may be formulated in carriers such as hydrophobic or hydrophilic bases to form ointments, creams, lotions, in aqueous, oleaginous or alcoholic liquids to form paints or in dry diluents to form powders. Such topical formulations can be used to treat ocular diseases as well as inflammatory diseases such as rheumatoid arthritis, psoriasis, contact dermatitis, delayed hypersensitivity reactions, and the like.

Certain embodiments of the invention are designed to locally deliver bioactive CAI into target eye tissue from implants to be injected in or around the eye, for sustained delivery of bioactive CAI to the eye. Alternatively, delivery vehicles are designed in the form of ointments, gels, viscous suspensions, or viscous emulsions that releases the drug upon administration into or around eye for prolonged periods to elicit the desired pharmacological action. The dosage form can also be a free flowing sterile suspension for topical administration or free flowing sterile suspensions for injection into or around eye.

When the CAI compound is formulated as a solution or suspension, the delivery system is in a pharmaceutically acceptable carrier, preferably a pharmaceutically acceptable aqueous carrier, suitable for local tissue compatibility. A variety of aqueous carriers may be used, e.g., water, buffered water, 0.8% saline, 0.3% glycine, hyaluronic acid and the like. Such delivery systems may be sterilized by conventional, well known sterilization techniques e.g., by heat or steam sterilization of formulations in sealed vials at about 130° C. for at least 15 minutes, or liquid formulations may be sterile filtered, e.g., by filtration through a 0.2 micron filter in a sterile pharmaceutic environment.

V. ROUTES OF ADMINISTRATION

The CAI compounds of the invention, and formulations thereof, can be used in a variety of routes of administration, including, for example, orally-administrable forms such as tablets targeting a specific local tissue e.g. gastrointestinal tissues, capsules or the like, or via injectable (e.g., parenteral, ocular, intravenous, subcutaneous, intramuscular), topical (e.g., dermal, ocular, transdermal, nasal), buccal, pulmonary (e.g., inhalation), suppository, or other route. In one embodiment, they can be in unit dosage form, namely, in physically discrete units suitable as unitary dosages for human consumption, each unit containing a predetermined quantity of active ingredient calculated to produce the desired therapeutic effect in association with one or more pharmaceutically acceptable other ingredients, i.e., diluent or carrier.

The routes of localized administration for the treatment of ocular diseases using the CAI compound or formulations thereof, of the invention include ophthalmic artery administration, subretinal injection, intravitreal injection, and periocular injection or juxtascleral administration. In the case of angiogenic diseases such as age-related macular degeneration and diabetic retinopathy, the formulations of the present invention are administered over a course of treatment ranging from weeks to years. The routes of administration for the treatment of such diseases include ophthalmic artery administration, subretinal injection, intravitreal injection, and periocular injection or juxtascleral administration. Sustained-release formulations such as implants would also be appropriate for the treatment of such long-term disease indications. These formulations may also be administered in combination with other anti-angiogenic agents.

In one embodiment of the invention, a CAI compound can be injected intraocularly using intravitreal (into the vitreous), subconjuctival (into the subconjuctival), subretinal (under the retina), or retrobulbar (behind the eyeball) injection. For subconjuctival injection, a CAI dose in the range of about 0.1 ng/ml to about 10 mg/ml may be used. For intravitreal injection, a CAI dose in the range of about 0.1 ng/0.1 ml to about 10 mg/0.1 ml may be used. For retrobulbar injection, a CAI dose in the range of about 1 ng/ml to about 10 mg/ml may be used. For subretinal injection, a CAI dose in the range of about 0.1 ng/0.1 ml to about 10 mg/0.1 ml may be used.

A. Time-Released Delivery Route

Slow or extended-release delivery systems, such as delivery systems comprising a biopolymer (biological-based systems), liposomes, colloids, resins, and other pharmaceutical acceptable polymeric delivery systems or compartmentalized reservoirs, can be utilized with the compositions described herein to provide a continuously releasing or long term releasing source of therapeutic compound. Such slow release systems are applicable to formulations for delivery via topical, intraocular, oral, and parenteral routes. Delivery to areas within the eye, in situ can be accomplished by injection such as by using a needle and syringe, by use of a cannula or other invasive device designed to introduce precisely metered amounts of a desired formulation to a particular compartment or tissue within the eye (e.g. anterior or posterior chamber, uvea or retina). A solid, semisolid, or liquid implant can be delivered subretinally using the instrumentation and methods described in U.S. Pat. Nos. 5,817,075 and 5,868,728, the contents of which are hereby incorporated by reference in their entirety.

Sustained-Release Systems Particularly Useful for the Treatment of Uveitis.

In certain embodiments of the invention, the CAI compound is formulated to be part of a sustained-release system. Such sustained release systems may be particularly useful for the treatment of uveitis, especially posterior infectious uveitis. Thus, in one embodiment, 5-amino-[4-(4-chlorobenzoyl)-3,5-dichlorobenzyl]-1,2,3-triazole-4-carboxamide may be formulated to be part of a sustained-release system. In another embodiment, the CAI compounds for Formula II or III may be formulated to be part of sustained-release system.

The sustained-release systems may be formulated to contain one or more of anti-inflammatory agent, an antibacterial agent, or a steroid (such as e.g. a glucocorticoid). As such, the sustained release systems may be suitable for use in combination therapy (see Combinatorial Therapies below). Thus, in one embodiment of the invention CAI alone or in combination with one or more of anti-inflammatory agent, an antibacterial agent, or a steroid in a sustained release system may be used to treat posterior infectious uveitis such as e.g. posterior infectious uveitis caused by toxoplasmosis, *toxocara* and visceral larva migrans.

The sustained-release system may be an implant. The implant may be a sustained release device or a sustained release-system that dissolves over time. In one embodiment, the sustained-release drug delivery system includes a polymer. In one embodiment, the polymer may be configured so that it dissolves over time (such as e.g. for up to 6 months) when implanted into the eye. In certain embodiments, the polymer may comprise a polylactic-coglycolic acid (PLGA). In a specific embodiment, the polymer may comprise poly (D,L-lactide-co-glycolide) PLGA. In one embodiment, the drug delivery system may also comprise a glucocorticoid. In one embodiment, the drug delivery system includes dexamethasone. The amount of dexamethasone in the system may vary. In certain embodiments, the amount of dexamethasone may range from about 0.1 to about 0.9 mg, alternatively from about 0.5 to about 0.8 mg, alternatively about 0.7 mg. In one embodiment, the CAI compound (e.g. 5-amino-[4-(4-chlorobenzoyl)-3,5-dichlorobenzyl]-1,2,3-triazole-4-carboxamide) is formulated to be part of an OZURDEX® (dexamethasone) intravitreal implant. Exemplary polymer sustained-release drug delivery system containing dexamethasone into which the CAI compound may be incorporated are disclosed in U.S. Pat. Nos. 6,726,918; 6,899,717; 7,033,605; 7,767,223; 8,034,366; 8,034,370; 8,043,628; 8,063,031; 8,088,407 and 8,506,987, the disclosures of which are incorporated in their entirety as they pertain to sustained-release drug delivery systems. In certain embodiments, the dexamethasone and CAI compound may be incorporated into a poly (D,L-lactide-co-glycolide) PLGA intravitreal polymer matrix. This matrix may be free of a preservative. In certain embodiments, the matrix may be the NOVADUR® solid polymer sustained-release drug delivery system.

The polymer sustained-release drug delivery system may have a variety of different configurations. In certain embodiments, the implant is rod shaped.

In one embodiment, the sustained-release drug delivery system is a device configured for implantation into the eye. Such devices may have a variety of shapes. In certain embodiments, the devices are injectable, non-erodible, intravitreal implants. Suitable sustained-release device are configured such that a pharmaceutically acceptable amount of CAI is released daily. In addition to CAI, these devices may also contain other pharmaceutically active compounds such as, for example, one or more of anti-inflammatory agent, an antibacterial agent, or a steroid (such as e.g. a glucocorticoid). In one embodiment, the device contains CAI and fluocinolone acetonide. Exemplary suitable sustained release devices are disclosed, for example, in U.S. Pat. Nos. 5,378,475; 5,773,019; 6,217,895; 6,375,972; 6,548,078; 8,252,307; 8,574,659 and 8,871,241, the disclosures of which are incorporated in their entirety as they pertain to sustained-release drug delivery devices. In one embodiment, the CAI compound (e.g. 5-amino-[4-(4-chlorobenzoyl)-3,5-dichlorobenzyl]-1,2,3-triazole-4-carboxamide) is formulated to be part of an ILUVIEN® (fluocinolone acetonide) intravitreal implant.

When used as part of a sustained-release drug delivery system, the CAI compound may be provided as a sonicated microparticle or in a molecular complex. In one embodiment, the CAI compound is provided as molecular complex in formulation with 1 to 60 wt % hydroxypropyl β-cyclodextrin and one or more of glutamate, L-phenylalanine, a cellulose derivative, a surfactant or combinations thereof. The cellulose derivate may be hydroxypropyl methyl cellulose.

In certain embodiments of the invention, the CAI compound is formulated to be part of a sustained-release system for the treatment uveitis, e.g. posterious infectious uveitis. When used in such a formulation, the amount of the CAI compound may range from about 100 to about 200 mcg, alternatively from about 150 to about 220 mcg, alternatively from about 150 to 200 mcg, alternatively about 150 mcg, or alternatively about 200 mcg.

In a time-release formulation, the microsphere, capsule, liposome, etc. may contain a concentration of CAI that could be toxic if it were administered as a bolus dose. The time-release administration, however, is formulated so that the concentration released over any period of time does not exceed a toxic amount. This is accomplished, for example, through various formulations of the vehicle (coated or uncoated microsphere, coated or uncoated capsule, lipid or polymer components, unilamellar or multilamellar structure, and combinations of the above, etc.). Other variables may include the patient's pharmacokinetic-pharmacodynamic parameters (e.g., body mass, gender, plasma clearance rate, hepatic function, genetic makeup, etc.). Depending upon the amount of CAI provided in the formulation and the release rate of the CAI, a patient could be dosed with CAI over a period of years from a single implant or injection comprising a CAI compound. As illustrative but non-limiting examples, a capsule or a device, e.g., for implantation use, can be loaded with a CAI-based formulation comprised of a concentration within the range of 1 to 200 mg of active CAI ingredient (e.g., 1 mg, 2 mg, 5 mg, 10 mg, 40 mg, 80 mg, 100 mg, 121 mg, 155 mg, 200 mg); if the capsule is formulated to release a few (e.g., 1 to 100) micrograms of CAI active ingredient drug per day, the patient's disease could be treated for a period ranging from about 7-1000 days (1-week to 3-years) via a single administration of the capsule or device. Such a formulation provides benefits which include accurate dosing with heightened patient convenience, because frequent intervention or administration is not required, rather administration can be done in some cases only once or twice a decade or even less frequently. The formation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz. London 2001, chapter 45); Handbook of Pharmaceutical Controlled Release Technology, Wise, Ed. (Marcel Dekker, New York 2000), the relevant sections of which are incorporated by reference herein in their entirety.

B. Dosage Forms

Depending on the clinical needs of a patient, formulations of the subject invention (see Section IV above) are prepared to either locally deliver the bioactive CAI immediately after administration or for bioactive CAI release into a target tissue (for example, eye tissue) from its vehicle in a sustained manner over a period of time suitable for the desired pharmacological action.

An effective quantity of the compound of interest is employed in treatment. The dosage of compounds used in accordance with the invention varies depending on the compound and the condition being treated. For example, the age, weight, and clinical condition of the recipient patient, and the experience and judgment of the clinician or practitioner administering the therapy are among the factors affecting the selected dosage. Other factors include the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer. In the case of angiogenic diseases such as age-related macular degeneration and diabetic retinopathy, the formulations of the present invention are administered over a course of treatment ranging from weeks to years.

C. Combinatorial Therapies

A further embodiment of the subject invention provides for the local administration of a CAI compound concurrently with other pharmacological therapies for the treatment of non-life threatening diseases. For example, a CAI compound of the invention can be administered concurrently with other clinical therapies such as the concurrent administration with anti-angiogenic compounds (e.g., combretastatin, angiostatin, endostatin, vitaxin, $2ME_2$, anecortave, squalamine, Macugen®, Lucentis®, PEDF), which may have diverse mechanisms of action (e.g. VEGF neutralization, tyrosine receptor kinase inhibition), glucocorticoids and non-steroidal anti-inflammatory drugs.

The present invention provides for the concurrent, localized administration of therapies and a CAI compound or formulations thereof, wherein the therapy addresses a non-life threatening disease (such as certain non-cancerous proliferative and angiogenic diseases) other than that treated by the CAI compound or formulations thereof, of the invention. For example, one embodiment of the invention provides the topical delivery of a CAI prodrug and novel formulations for treating severe dermatological diseases including severe psoriasis, excema and rosacea and local intrarticular administration for severe arthritis by inhibiting vascular and inflammatory cell proliferation.

A further embodiment of the subject invention provides for the treatment of neovascular and edematous ocular diseases by ocular administration of a CAI compound, as described herein, in combination with other pharmacological anti-angiogenesis therapies. Contemplated anti-angiogenesis therapies comprise those which include, but are not limited to, glucocorticoids (such as, dexamethasone, fluorometholone, administration of medrysone, budesonide, betamethasone, fluocinalone, triamcinolone, triamcinolone acetonide, prednisone, prednisolone, hydrocortisone, rimexolone, and pharmaceutically acceptable salts thereof), anecortave acetate, VEGF-binding molecules (oligonucleotide aptamers (e.g. Macugen®), protein antibodies (e.g. Lucentis®), tyrosine receptor kinase inhibitors including but not limited to vascular endothelial growth factor (VEGF), platelet derived growth factor (PDGF) and fibroblast growth factor (FGF) receptors, other direct or indirect growth factor inhibitors including somatostatin receptor agonists (inhibiting release of Growth Hormone and IGF-1), RNAi oligonucleotide transcription inhibitors of ocular disease molecular targets including growth factors described above.

Active agents suitable for concurrent administration with a CAI compound or formulation thereof include, but are not limited to, anti-infectives, including, without limitation, antibiotics, antivirals, and antifungals; antiallergenics and mast cell stabilizers; steroidal and non-steroidal anti-inflammatory agents; cyclooxygenase inhibitors, including, without limitation, Cox I and Cox II inhibitors; combinations of anti-infective and anti-inflammatory agents; anti-glaucoma agents, including, without limitation, adrenergics, beta-adrenergic blocking agents, α-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of the posterior segment of the eye, including, without limitation, ARMD, CNV, retinopathies, retinitis, uveitis, macular edema, and glaucoma. Such angiostatic steroids are more fully disclosed in U.S. Pat. Nos. 5,679,666 and 5,770, 592, which are incorporated herein in their entirety by reference. Preferred ones of such angiostatic steroids include 4,9(11)-Pregnadien-17α,21-diol-3,20-dione and 4,9(11)-Pregnadien-17α,21-diol-3,20-dione-21-acetate. A preferred non-steroidal anti-inflammatory for the treatment of cystoid macular edema is nepafenac.

A further embodiment of the subject invention provides for treatment of proliferative and edematous diseases via concurrent administration of a CAI compound and an anti-angiogenic compound. Diverse anti-angiogenic compounds can be used in a combinatorial treatment of the invention, include those with diverse mechanisms of action (e.g. VEGF neutralization, tyrosine receptor kinase inhibition, arachidonate inhibition, and Bcl-2 upregulation), such as glucocorticoids, non-steroidal anti-inflammatory drugs.

A further embodiment of the subject invention provides for the local administration of CAI compound and related formulations thereof, in combination with other pharmacological therapies specifically designed to provide efficacy with limited side effects, e.g. neuroprotectant agents, inhibitors of drug efflux, metabolite inhibition, synergistic agents, and agents designed to decrease specific side effects.

A further embodiment of the subject invention provides for the treatment of ocular diseases such as glaucoma and inflammatory eye disease by ocular administration of CAI compound or formulations thereof, as described herein in combination with other pharmacological agents including, but are not limited to, verteporfin photodynamic therapy (QLT Pharmaceuticals), anecortave acetate (Alcon Research Ltd.), Macugen® (Eyetech Pharmaceuticals), Lucentis® (ranibizumab, Genentech), Squalamine lactate (Genaera Corporation), LY333531 (Eli Lilly), and Fluocinolone (Bausch & Lomb), timolol, bromodidine, cyclosporine, cisplatin, carboplatin, methotrexate, steroids, BDNF, CTF, and TNF-α blockers such as thalidomide and its derivatives and prodrugs.

Dexamethasone has been detected at 13 ng/ml in the vitreous cavity following a single 5 mg peribulbar injection in humans (Weijtens et al. *Ophthalmology* 107(10): 1932-8 2000; Weijtens et al. *Am J Ophthalmol* 128(2): 192-7 1999). This results in a vitreous concentration of approximately 0.10-0.13 µM assuming a vitreous volume of 4-5 ml. Delivery to the subretinal space is 10-fold higher following subconjunctival injection (Weijtens et al. *Am J Ophthalmol* 123(3): 358-63 (1997)). The serum half-life of dexamethasone (18-36 hours) is significantly shorter than that of CAI (111 hours). Physiological tissue concentrations of CAI are in the 1-10 µM range so that it appears reasonable to postulate based on the scleral permeability and prolonged serum half-life of CAI that it can be effectively delivered transsclerally to the subretinal space, and the vitreous cavity in physiological concentrations (Weijtens et al. *Ophthalmology* 107(10): 1932-8 2000; Weijtens et al. *Am J Ophthalmol* 128(2): 192-7 1999). The release rates of CAI compound or formulations thereof, from sustained-release devices are also favorable. One potential drawback of the intravitreal implants that were constructed with CAI was that some demonstrated rapid expansion because of the hygroscopic nature of CAI (Weijtens et al. *Am J Ophthalmol* 123(3): 358-63 1997). This rapid expansion may be alleviated by developing a non-aqueous reservoir for the CAI compound or formulations thereof, pellet, or by formulations of a prodrug as stated in this patent.

The present invention also contemplates the use of a glucocorticoid and/or neuroprotective agent in combination with the CAI compound or formulations thereof. A glucocorticoid alone and/or neuroprotective agent in combination with CAI compound or formulations thereof, is useful for treating persons suffering from pathologic ocular angiogenesis, in particular, exudative ARMD and/or PDR, as well as subretinal or retinal edema associated with either condition. In addition to being effective in inhibiting the neovascularization associated with wet ARMD and PDR, CAI compound or formulations thereof, could be useful in controlling any TOP rise associated with the use of a glucocorticoid, or to protect the retina from ischemic damage associated with microangiopathy or retinal vascular occlusions.

The present invention also contemplates the use of a glucocorticoid and/or neuroprotective agent in combination with the CAI compound (e.g. 5-amino-[4-(4-chlorobenzoyl)-3,5-dichlorobenzyl]-1,2,3-triazole-4-carboxamide) or formulations thereof for use in the treatment of uveitis, in particular posterior infectious uveitis. For example, in one embodiment, the CAI compound may be used in combination with a glucocorticoid (exemplary glucocorticoids include, dexamethasone, fluoromethalone, administration of medrysone, budesonide, betamethasone, fluocinalone, triamcinolone, triamcinolone acetonide, prednisone, prednisolone, hydrocortisone, rimexolone, and pharmaceutically acceptable salts thereof). In one embodiment, the CAI compound is used in combination with dexamethasone. In another embodiment, the CAI compound may be used in combination with the glucorticoid and an anti-inflammatory agent.

D. Delivery Via Devices

A further embodiment provides the use of CAI compound or formulations thereof, in conjunction with a drug delivery system in the form of an implant or a device for treatment of conditions as set forth herein.

The present invention also provides CAI compound or formulations thereof, for use as coatings in conjunction with physical material implants such as stents and band ligatures used to treat vascular diseases. In an embodiment, novel CAI compound or formulations thereof, coated stents of the subject invention are used in the treatment of vascular disorders such as restenosis or vascular occlusion following vascular insult (e.g., angioplasty, allo- or xenotransplant vasculopathies; variceal bleeding, and transplantation of an organ).

Delivery of drugs in the form of topical eye drops is also of little utility when the drug is a protein or peptide that lacks the ability to cross the cornea and be made available to the vitreous, retina, or other subretinal structures such as the retinal pigment epithelium ("RPE") or choroidal vasculature. An extraocular insert is a contact lens delivery system that releases medication over an extended period. The lens generally only lasts for a matter of hours or days before dissolving or releasing all of the therapeutic compound. Continuous delivery of medication is inconvenient, requiring frequent re-application. Again, these contact lenses only provide drug to the cornea and anterior chamber.

In rare cases, direct delivery of drugs has also been accomplished using extemraliz tubes. This requires insertion of one end of a tube into the corner of the patient's eye. The other end of the tube is taped to the patient's forehead and terminates in a septum, through which medication is delivered. This method is undesirable, being both uncomfortable and inconvenient. Since medication must be injected through the septum, the device is incapable of continuous delivery of medication. Furthermore, such tubes may become infected and in some cases ultimately threaten the patient's vision. Direct delivery of drugs can also be accomplished by the intraocular injection of the drug, or of microspheres that contain or comprise the drug. However, microspheres tend to migrate within the eye, either into the visual axis or into adjacent tissue sites.

An intraocular insert is currently available for delivery of ganciclovir to the eye. Known as Vitrasert, the device consists of a nonerodible, polymer-based, sustained-release package containing ganciclovir, and a non-proteinaceous nucleoside analog. The device is surgically implanted in the vitreous humor of the eye to treat cytomegalovirus retinitis. See, e.g., Anand, R., et al., Arch. Ophthalmol., 111: 223-227 (1993). Another intraocular insert is disclosed by U.S. Pat. No. 5,466,233. This tack-shaped device is surgically implanted so that the head of the tack is external to the eye, abutting the scleral surface. The post of the tack crosses the sclera and extends into the vitreous humor, where it provides for vitreal drug release.

CAI compound or formulations thereof, of the invention may be administered surgically as an ocular implant. As one example, a reservoir container having a diffusible wall of polyvinyl alcohol or polyvinyl acetate or partially hydrolyzed (e.g., about 1% to about 99% hydrolyzed) polyvinyl acetate and containing milligram (e.g., in the range of from about 1 mg to about 100 mg) quantities of CAI may be implanted in or on the sclera. As another example, CAI in milligram quantities may be incorporated into a polymeric matrix having dimensions of about 2 mm by 4 mm, and made of a biocompatible and optionally biodegradable polymer such as polycaprolactone, poly(glycolic) acid, poly(lactic) acid, or a polyanhydride, or a lipid such as sebacic acid, and may be implanted on the sclera or in the eye. This is usually accomplished with the patient receiving either a topical or local anesthetic and using a small (3-4 mm incision) made behind the cornea. The matrix, containing CAI compound or formulations thereof, is then inserted through the incision and sutured to the sclera using 9-0 nylon.

For example, U.S. Pat. No. 5,773,019, the contents of which is hereby incorporated by reference, discloses implantable controlled release devices for delivering drugs to the eye wherein the implantable device has an inner core containing an effective amount of a low solubility drug covered by a non-bioerodible polymer coating layer that is permeable to the low solubility drug. U.S. Pat. No. 5,378,475, the contents of which is hereby incorporated by reference, discloses sustained-release drug delivery devices that have an inner core or reservoir comprising a drug, a first coating layer which is essentially impermeable to the passage of the drug, and a second coating layer which is permeable to the drug. The first coating layer covers at least a portion of the inner core but at least a small portion of the inner core is not coated with the first coating layer. The second coating layer essentially completely covers the first coating layer and the uncoated portion of the inner core. U.S. Pat. No. 4,853,224, the contents of which is hereby incorporated by reference, discloses biodegradable ocular implants comprising microencapsulated drugs for implantation into the anterior and/or posterior chambers of the eye.

The polymeric encapsulating agent or lipid encapsulating agent is the primary element of the capsule. U.S. Pat. No. 5,164,188, the content of which is hereby incorporated by reference, discloses the use of biodegradable implants in the suprachoroid of an eye. The implants are generally encapsulated. The capsule, for the most part, is a polymeric encapsulating agent. Material capable of being placed in a given area of the suprachoroid without migration, "such as oxycel, gelatin, silicone, etc." can also be used. U.S. Pat. No. 6,120,789, the contents of which is hereby incorporated by reference, discloses the use of a non-polymeric composition for in situ formation of a solid matrix in an animal, and use of the composition as a medical device or as a sustained-release delivery system for a biologically-active agent, among other uses. Such implants can provide CAI compound or formulations thereof, of the invention to a patient to treat a non-life threatening disease.

Another implantable device that can be used to deliver formulations of the present invention is the biodegradable implants described in U.S. Pat. No. 5,869,079, the contents of which is hereby incorporated by reference. Additional intracorporeal devices to which a CAI compound or formulations thereof, can be added for example in the form of a coating include, but are not limited to, catheters, stents, angioplasty balloons, pacemakers, etc.

Within yet other aspects of the present invention, methods are provided for expanding the lumen of a body passageway, comprising inserting a stent into the passageway, the stent having a generally tubular structure, the surface of the stent structure being coated with a composition comprising a CAI compound, optionally in the presence of paclitaxel, such that the passageway is expanded. Within various embodiments of the invention, methods are provided for eliminating biliary obstructions, comprising inserting a biliary stent into a biliary passageway; for eliminating urethral obstructions, comprising inserting a urethral stent into a urethra; for eliminating esophageal obstructions, comprising inserting an esophageal stent into an esophagus; and for eliminating tracheal/bronchial obstructions, comprising inserting a tracheal/bronchial stent into the trachea or bronchi. Within each of these embodiments the stent has a generally tubular structure, the surface of the structure being coated with a composition comprising a CAI compound or formulation thereof and, optionally, together with other pharmaceutically active agents for a combination therapy.

VI. ANIMAL EFFICACY AND SAFETY MODELS

The CAI parent compound, and the principles on which the CAI compound or formulations thereof, of the inventions described herein, have been demonstrated to have antiproliferative and antimetastatic activity that was linked to decrease of intracellular calcium by inhibition of non-voltage-gated calcium channels. Furthermore, the anti-angiogenic activity of CAI, the active ingredient contained in the CAI compound or formulations thereof, or applied via drug delivery systems and routes of administration that are the subject of this invention, conferring efficacy on neovascular disease has been well established.

The CAI compound or formulations thereof, used directly or in conjunction with a drug delivery method or device as described herein have highly advantageous therapeutic efficacy and safety for clinical use as local disease therapy when compared to systemic therapies of CAI described to date. The advantages of the CAI compound or formulations thereof, and administration methods of this invention are provided by the controlled, efficacious, and safe free CAI drug concentrations to the target tissue. The efficacy of CAI compound or formulations thereof, and drug delivery systems described herein to treat diseases described herein can be confirmed using standard in vivo animal test model of disease. These models include the mouse retinal neovascularization retinopathy of prematurity model (Smith L E et al. Invest Ophthalmol Vis Sci. 35(1):101-11, 1994, the method of which is hereby incorporated by reference), as well as the demonstration of an antiproliferative effect on choroidal endothelial cells and RPE in culture (Hoffman et al. Oph-

*thalmologe* 2004, the method of which is hereby incorporated by reference). Further, the ability of CAI compound or formulations thereof, to provide controlled, safe levels suitable to treat human proliferative or neovascular ocular diseases can be confirmed using standard in vivo animal test ocular pharmacokinetic and pharmacodynamic studies in animals.

The CAI parent compound active ingredient from which the CAI compound or formulations thereof, inventions described herein derive, has demonstrated primary pharmacological action to decrease intracellular calcium concentration by inhibition of non-voltage-gated calcium channels (Kohn, E. C. et al. *CAI. Cancer Res.* 54:935-942, 1994) thus affecting diverse signal transduction processes. Furthermore, the pharmacological mechanisms of action of CAI include (but are not limited to) the inhibition of disease mediating molecules including growth factors (e.g. VEGF), cytokines (e.g. IL-6), matrix metalloproteinases (MMps) and arachadonic acid (Felder, C. C. et al. *J Pharmacol Exp Ther.* 257:967-971, 1991; Fox D A et al. *Ann N Y Acad Sci.;* 893:282-5, 1999; Cole K. et al. *Cancer Metastasis Rev.* March; 13(1):31-44, 1994). These pharmacological mechanisms described for CAI provide the fundamental basis of anti-proliferative activity on diverse cancer cell types (melanoma, breast, squamous, prostate, ovarian, glioblastoma, colon, and small lung cell cancer) relevant to current clinical application of CAI as a systemically administered drug in life-threatening cancer indications. Furthermore, these pharmacological mechanisms described for CAI provide the fundamental basis of anti-proliferative activity against other non-cancer cell types directly relevant to the invention, including but not limited to, human vascular and retinal endothelial cells, retinal pigment and choroidal endothelial cells (Hoffman et al. *Ophthalmologe* 2004), inflammatory cells including lymphocytes and eosinophils. Furthermore, since pathological increases in intracellular calcium (e.g. as mediated by pathological activation of NMDA receptor channels by excess glutamate in ischemic conditions) in neurons is known to result in neuronal death, it is anticipated by this invention that administration of CAI compound or formulations thereof, as described herein can be neuroprotective. Therefore, based on the pharmacological mechanisms CAI compound or formulations thereof, described herein have anti-angiogenic, anti-inflammatory and neuroprotective effects associated with the treatment of diseases of relevant diseases as described herein.

The CAI compound or formulations thereof, used directly or in conjunction with a drug delivery method or device as described herein have highly advantageous therapeutic efficacy and safety for clinical use as local disease therapy when compared to systemic therapies of CAI described to date. The advantages of the CAI compound or formulations thereof, and administration methods of this invention are provided by the controlled, efficacious, and safe free CAI drug concentrations administered to or reaching the target tissue. Plasma concentrations of CAI that have been associated with efficacy in cancer described in patients range from approximately 1.0 to 10 micromolar while plasma concentrations of above 100 micromolar can be associated with unacceptable toxicity. The invention anticipates pharmacologically active concentrations of CAI as provided by the CAI compound or formulations thereof, of this invention to exhibit therapeutic effects in the local target tissue to range between 0.5 and 100 micro molar. As a specific example this invention anticipates periocular administration of a CAI compound or formulations thereof, which formulations contain 5 mg of active CAI ingredient, to provide CAI to the target subretinal and vitreal compartments in concentrations ranging from 0.1 and 10 micromolar concentration over a one-day time period. The ability of CAI compound or formulations thereof, to provide controlled, safe levels suitable to diseases described herein can be confirmed using standard in vivo pharmacokinetic studies in healthy animals or animal disease models. The CAI compound or formulations thereof, is administered as described herein and the samples of the target tissue are analyzed for concentration of CAI active principle using known e.g., (Tutsch, K. D. et al. *Proc Am Assoc Cancer Res.* 37:A1133, 1996, the contents of which are hereby incorporated by reference in their entirety) or tissue adapted bioanalytical methods. For example, a CAI formulation containing 5 mg of active CAI ingredient is given to rabbits by periocular administration, and the animals are sacrificed at different time points over a 24 hour period. Tissue and liquid humor samples are taken from the eyes and the CAI active ingredient is extracted and subjected to HPLC-MS analysis with an appropriate internal standard to the target disease compartments including retinal, choroidal and vitreal compartments.

The efficacy of CAI compound or formulations thereof, alone or in conjunction with drug delivery systems described herein to treat diseases described herein can be confirmed using in vivo animal test models of disease. These models include the mouse retinal neovascularization retinopathy of prematurity model (Smith L E et al. *Invest Ophthalmol Vis Sci.* 35(1):101-11, 1994, the methods of which are hereby incorporated by reference). In this model, mouse pups are placed into 75% $O_2$, along with their nursing dams, at post-natal day 7. They are maintained at this oxygen level for five days, at which point they are returned to normoxia. For the next five days, the pups are administered with CAI compound or formulations thereof, using the methods described herein. At day 17, the animals are euthanized, enucleated, and the eyes fixed in 4% buffered paraformaldehyde overnight, then transferred to saline, embedded in paraffin, and sectioned. Serial sections are collected (6 micron sections, every $30^{th}$ section) and stained with hematoxylin and eosin. Individuals masked to the identity of treatment then count the number of pre-retinal nuclei and the effects of CAI compound or formulations thereof, on lowering the number of pre-retinal nuclei are evaluated relative to control. At least eight sections are counted for each eye. Another model is the adult mouse model of ischemia-induced choroidal neovascularization that mimics age-related macular degeneration. In this model, adult mice are subjected to laser photocoagulation in a manner similar to Ryan's (Ryan S J. et al. *Trans Am Ophthalmol Soc.* 77:707-745, 1979, the methods of which are hereby incorporated by reference). Three burn spots are produced in the choroid using an argon green wavelength laser at a power of 910-1030 mW for 0.05 sec to induce choroidal rupture and subsequent neovascularization. The burns are in three quadrants of the choroid, one disc area in diameter and one disc area from the optic nerve. This fixed distance allows the burns to be both reproducible and isolated from each other. The laser produces a bubble in the majority of cases, which is indicative of a Bruch's membrane rupture. In less than 5% of the animals, bleeding may be noted upon treatment. The mice are euthanized at two weeks after receiving laser photocoagulation and the eyes removed for evaluation of choroidal neovascularization.

Other disease models include xenograft models for host vs. graft tissue rejection relevant to applications including restenosis. Another object of the present invention is to provide for local treatment of other proliferative and angiogenic diseases including topical delivery of CAI compound or formulations thereof, for severe dermatological diseases including severe psoriasis, excema and rosacea and local intrarticular administration for severe arthritis by inhibiting vascular and inflammatory cell proliferation.

VII. THERAPEUTIC APPLICATIONS

In one embodiment, the CAI compound and formulations thereof of the present invention can be used for administration to a human patient suffering from a non-life threatening disease, as a method of treatment of such disease. The non-life threatening disease can be, for example a proliferative disease, an inflammatory disease, an edematous disease, a neurodegenerative and/or a neurotoxic disease, or a signal transduction-mediated disease, or a matrix metalloproteinase-mediated disease.

Examples of diseases or disorders that can be mediated directly, or indirectly, by the administration of a CAI compound or formulations thereof, of the invention include, but are not limited to: age-related macular degeneration, diabetic retinopathy, retinal vascular occlusion, choroidal and retinal angiomatous proliferation, chronic glaucoma, retinal detachment, sickle cell retinopathy, rubeosis iridis, uveitis, neoplasms, Fuchs heterochromic iridocyclitis, neovascular glaucoma, corneal neovascularization, neovascularization resulting from combined vitrectomy and lensectomy, retinal ischemia, choroidal vascular insufficiency, choroidal thrombosis, carotid artery ischemia, retinal artery/vein occlusion, e.g., central retinal artery occlusion and branch retinal vein occlusion, contusive ocular injury, and retinopathy of prematurity, and other vascular anomalies, e.g., retinitis pigmentosa, endophthalmitis, infectious diseases, inflammatory but non-infectious diseases, ocular ischemia syndrome, peripheral retinal degenerations, retinal degenerations and tumors, choroidal disorders and tumors, vitreous disorders, retinal detachment, non-penetrating and penetrating trauma, post-cataract complications, and inflammatory optic neuropathies.

In one embodiment, the disease that can be mediated directly, or indirectly, by the administration of a CAI compound or formulations thereof may be uveitis or any other inflammation of the uvea. In particular, the CAI compound or formulations may be used to treat infectious uveitis. In one embodiment, the CAI compound may be used to treat infectious posterior uveitis (e.g. inflammation of the retina or choroid). In certain embodiments, the infectious posterior uveitis may be due to parasites or bacteria. For example, infectious uveitis may encompass inflammation of the uvea associated with one or more of toxoplasmosis, bartonellosis, histoplasmosis, Lyme disease, syphilis, and tuberculosis.

Hereditary degenerative retinal and vitreoretinal diseases treatable with a CAI compound or formulations thereof, of the invention, either alone or in combination therapies, include: Primary pigmented retinopathies, all gene types (ocular involvement only); Autosomal dominant retinitis pigmentosa e.g. rod-cone and cone-rod degenerations; Autosomal recessive retinitis pigmentosa e.g. rod-cone and cone-rode degenerations, Leber's amaurosis congenita; X-linked recessive pigmented retinopathies e.g. choroideremia; Secondary pigmented retinopathies (retinopathies associated with systemic diseases); Autosomal dominant pigmented retinopathies, e.g. Paget's disease, Charcot-Marie-Tooth disease, Steinert's disease, Pierre-Marie syndrome; Autosomal dominant pigmented retinopathies e.g. diabetes mellitus, mannosidoses, mucopolysccharidoses, Batten's disease, Refsum's disease, Usher syndrome; X-linked recessive pigmented retinopathies e.g. Hunter syndrome; conjunctivitis (e.g. allergic conjunctivitis, chronic conjunctivitis, contact lens-associated conjunctivitis, conjunctival ulceration, drug-related conjunctivitis); uveitis, uveoretinitis, chronic diseases (e.g. age-related macular panuveitis, retinitis, degeneration diabetes mellitus, infectious choroiditis, vitreitis, diseases (e.g., tuberculosis syphilis, cytomegalo-Scleritis/Episcleritis, virus retinitis), injury as a result of physical agents (e.g. UV Iridocyclitis, radiation), chemical agents (e.g. acids, Endophthalmitis, caustic solvents), and immunological etiologies (e.g. sarcoidosis, inflammatory bowel disease, Corneal ulceration disease, and other collagen vascular diseases). Von Hippel-Lindau syndrome is a specific neovascular disease that has both ocular and non-ocular manifestations that should be treatable by CAI compounds and formulations thereof.

The compounds, formulations, and methods of the present invention may also be used to treat ocular symptoms resulting from diseases or conditions that have both ocular and non-ocular symptoms. Some examples include AIDS-related disorders such as cytomegalovirus retinitis and disorders of the vitreous; pregnancy-related disorders such as hypertensive changes in the retina; and ocular effects of various infectious diseases such as tuberculosis, syphilis, lyme disease, parasitic disease, *toxocara canis*, ophthalmonyiasis, cyst cercosis, and fungal infections. Non-ocular diseases can also include rheumatoid arthritis, psoriasis, contact dermatitis, keratitis, conjunctivitis, scleritis, squamous cell carcinoma and condyloma.

Angiogenesis and neovascularization in the adult animal is usually a pathological process, and is in direct contradistinction to non-pathological neovascularization, which usually occurs in normal embryogenesis (e.g., development of the embryonic vascular system). In accordance with the subject invention, neovascularization refers specifically to pathological neovascularization. Aberrant or pathological vascularization is a key component in numerous disease states. For example, vascularization is a critical element of most solid tumors, such as cancers of the brain, genitourinary tract, lymphatic system, stomach, larynx and lung. These include histiocytic lymphoma, lung adenocarcinoma and small cell lung cancers. Aberrant vascular growth in the retina can lead to visual degeneration, which can culminate in blindness. Accordingly, the subject invention provides CAI compound and formulations thereof for the treatment of neovascularization.

Compounds of the invention can also be used to inhibit the proliferation of vascular endothelial cells and so are indicated for use in treating graft vessel diseases such as restenosis or vascular occlusion following vascular insult such as angioplasty, allo- or xenotransplant vasculopathies, graft vessel atherosclerosis, and in the transplantation of an organ (e.g., heart, liver, lung, kidney or pancreatic transplants (Weckbecker et al., *Transplantation Proceedings* 1997, 29, 2599-2600).

The present invention also provides for the treatment of severe dermatological diseases including severe psoriasis, contact dermatitis, excema and rosacea; severe arthritis; and other vascular and inflammatory cell proliferative diseases (such as rheumatoid arthritis; spondyloarthropathies; gouty arthritis; osteoarthritis; systemic lupus erythematosus; juvenile arthritis; asthma; bronchitis; menstrual cramps; tendonitis; bursitis; skin related conditions such as psoriasis, eczema, burns, and dermatitis; gastrointestinal conditions such as inflammatory bowel disease, Crohn's disease, gastritis, irritable bowel syndrome and ulcerative colitis; colorectal cancer; migraine headaches; periarteritis nodosa; thyroiditis; aplastic anemia; Hodgkin's disease; scleredoma; rheumatic fever; type I diabetes; myasthenia gravis; sarcoidosis; nephrotic syndrome; Behcet's syndrome; polymyositis; gingivitis; hypersensitivity; swelling occurring after injury; myocardial ischemia; and the like).

Additionally, disease states which rely on aberrant signal transduction/proliferation may also be treated by the CAI compound or formulations thereof, or methods of the invention. Diseases of potentially aberrant signal transduction/proliferation may include the collagen vasculitides (i.e., systemic lupus erthythematosis and rheumatoid arthritis), neurologic diseases (i.e., dementia and nerve conduction diseases), diseases of transport (i.e., cystic fibrosis), toxic effects of agents (i.e., cisplatin-related neuropathy), and cellular dysfunction (i.e., myelodysfunction syndromes), hemangiomata, and collagen vasculidities.

One embodiment of the subject invention provides for the local ocular administration of CAI compound or formulations thereof, by means of periocular, retrobulbar, intravitreal, subretinal, posterior juxtascleral, topical and subconjunctival administration through injection or needle-free system, or topical administration though local instillation, drops, ointment, or in conjunction with drug delivery systems exemplified by contact lenses, devices and implants. A related embodiment provides the treatment of a broad range of ocular diseases including diabetic retinopathy (DR), neovascular proliferative age-related macular degeneration (ARMD), diabetic macular edema (DME), cystoid macular edema (CME) and ocular tumors such as retinoblastoma (RB), Retinopathy of Prematurity (ROP), retinal vascular occlusions (RVO), uveitis, glaucoma, corneal neovascularization, iris neovascularization, neovascular glaucoma, ischemic neural damage, and pterygium by the local ocular administration of CAI compound and related formulations thereof, directly or in conjunction with a drug delivery system as described herein.

Following are examples, which illustrate procedures for practicing the invention. These examples should not be construed as limiting.

It is advantageous to define several abbreviations before describing the examples. It should be appreciated that the following abbreviations are used throughout this application.

CAI=5-amino-[4-(4-chlorobenzoyl)-3,5-dichlorobenzyl]-1,2,3-triazole-4-carboxamide
Tween® 80=polyoxyethylenesorbitan monooleate
Pluronic®=polyoxyethylene-polyoxypropylene block copolymer
Pluronic® F-68, F-127=α-hydro-omega-hydroxypoly(oxyethylene)-poly(oxypropylene)-polyoxyethylene block copolymers Example 1

Procedures for Preparing and Identifying Stable, Autoclavable Aqueous Formulations of CAI Compounds General Procedure Amorphous solid free base form of CAI active pharmaceutical ingredient having Formula I (5-amino-[4-(4-chlorobenzoyl)-3,5-dichlorobenzyl]-1,2,3-triazole-4-carboxamide), which can be synthesized by one skilled in the art of organic chemistry according to procedures described in U.S. Pat. Nos. 4,590,201 and 5,602,156, is first dissolved in a minimal volume of absolute ethanol at 40° C. Additives are added to this solution as selected from an ionic surfactant (preferably a lipophilic organic acid having at least 8 carbon atoms such as oleic acid), an organic oil, such as alkyl ester of fatty acid and/or monoglyceride, diglyceride, or triglyceride, or glyceride (e.g. soybean oil, or mixtures thereof), and other organic solubilizing additives (e.g. Tweens, Pluronics, cyclodextrins, polysorbates, sorbitan esters, sucroesters, and other non-ionic surfactants, polyethylene glycols, particularly those that are liquid at ambient temperature) in proportions that result in a clear solution containing CAI in concentrations from 1 to 200 mg/mL. Preferred proportions of these primary formulation ingredients are selected based on suitability for achieving concentrations of CAI from 1 to 100 mg/mL. After adding water to the resulting organic solution of CAI a stable organic-aqueous mixture comprising CAI results as a homogeneous solution, stable emulsion, or self-emulsifying dry powder. The ethanol is removed from the resulting organic mixture described above by evaporation (e.g. under reduced pressure using a rotary evaporator). Water is added to the resulting organic mixture, and the pH is adjusted to an acceptable therapeutically applicable range (preferably from about pH 3.0 to about pH 8.0 and more preferably from about pH 5.0 to about pH 8.0). The exact pH adjustment is done by addition of a basic solution (preferably aqueous sodium hydroxide) or an acidic solution (preferably aqueous hydrochloric acid) or both in quantities sufficient to provide the desired pH.

Preliminary preferred formulations are first selected by simple inspection based on stability of the final solution against separation into distinct organic and aqueous phases after standing for at least 3 days within an ambient temperature range. Formulations that phase separate are unstable and are discarded. Stable sterile formulations are then prepared by autoclaving for sufficient time at temperatures suitable for effectively killing the microorganisms that may be present in the formulation, for instance, 121° C. for about 30 minutes.

An alternate method for manufacturing stable sterile formulations can be readily accomplished by filtration through sterile filtration membranes (e.g., 0.1 micron membranes, 0.2 micron membranes).

Formulation 1

Formulation 1 is prepared according to the General Procedure described in Example 1 using the following amounts of reagents or corresponding relative proportions: CAI free base (50 mg), oleic acid (150 mg), soybean oil (150 mg), Tween®-80 (100 mg), Pluronic® F-68 (100 mg). A creamy emulsion of milky white appearance is formed after dilution with water to a final CAI concentration of 36 mg/mL (3.6%). The emulsion of Formulation 1 is stable based on stability to phase separation as defined in Example 1. The active CAI ingredient is stable to autoclave sterilization conditions of 121° C. at a pressure of 15 psi as defined in Example 1. Thus, after autoclaving Formulation 1 under these conditions for 30 min no decomposition of CAI or formation of new impurities could be detected by reverse phase high pressure liquid chromatography (RP-HPLC) analysis using UV detection (Conditions: RP-18 column: 5μ particle size, length=13 cm, diameter=8 mm; solvent system: solvent A=0.001% trifluoroacetic acid, solvent B=acetonitrile, gradient=80% A/20% B to 10% A/90% B over 12 min at a flow rate of 2.5 mL/min; CAI retention time=6.3 min).

Formulation 2

Formulation 2 is prepared according to the General Procedure described in Example 1 using the following amounts of reagents or corresponding relative proportions: CAI free base (50 mg), oleic acid (200 mg), soybean oil (200 mg) and Tween®-80 (100 mg). An emulsion of milky white appearance is formed after dilution with water to a final CAI concentration of 60 mg/mL (6.0%). The emulsion of Formulation 2 is stable based on stability to phase separation at ambient temperature. The active CAI ingredient is stable to autoclave sterilization conditions of 121° C. at a pressure of 15 psi as defined in Example 1. Thus, after autoclaving Formulation 2 under these conditions for 30 min no decomposition of CAI or formation of new impurities could be detected by RP-HPLC analysis using UV detection (Conditions: RP-18 column: 5µ particle size, length=13 cm, diameter=8 mm; solvent system: solvent A=0.001% trifluoroacetic acid, solvent B=acetonitrile, gradient=80% A/20% B to 10% A/90% B over 12 min at a flow rate of 2.5 mL/min; CAI retention time=6.3 min).

Formulation 3

Formulation 3 is prepared according to the General Procedure described in Example 1 using the following amounts of reagents or corresponding relative proportions: CAI free base (50 mg), oleic acid (300 mg), Pluronic® F-127 (100 mg) and Tween®-80 (100 mg). A creamy emulsion of milky white appearance is formed after dilution with water to a final CAI concentration of 36 mg/mL (3.6%). The emulsion of Formulation 3 is stable based on stability to phase separation at ambient temperature. The active CAI ingredient is stable to autoclave sterilization conditions of 121° C. at a pressure of 15 psi as defined in Example 1. Thus, after autoclaving Formulation 3 under these conditions for 30 min no decomposition of CAI or formation of new impurities could be detected by RP-HPLC analysis using UV detection (Conditions: RP-18 column: 5µ particle size, length=13 cm, diameter=8 mm; solvent system: solvent A=0.001% trifluoroacetic acid, solvent B=acetonitrile, gradient=80% A/20% B to 10% A/90% B over 12 min at a flow rate of 2.5 mL/min; CAI retention time=6.3 min).

Formulation 4

Formulation 4 is prepared according to the General Procedure described in Example 1 using the following amounts of reagents or corresponding relative proportions: CAI free base (50 mg), oleic acid (150 mg), soybean oil (150 mg), Pluronic® F-68 (100 mg) and Tween®-80 (100 mg). A creamy emulsion of milky white appearance is formed after dilution with water to a final CAI concentration of 36 mg/mL (3.6%). The emulsion of Formulation 4 is stable based on stability to phase separation at ambient temperature. The active CAI ingredient is stable to autoclave sterilization conditions of 121° C. at a pressure of 15 psi as defined in Example 1. Thus, after autoclaving Formulation 4 under these conditions for up to 30 min no decomposition of CAI or formation of new impurities could be detected by RP-HPLC analysis using UV detection (Conditions: RP-18 column: 5µ particle size, length=13 cm, diameter=8 mm; solvent system: solvent A=0.001% trifluoroacetic acid, solvent B=acetonitrile, gradient=80% A/20% B to 10% A/90% B over 12 min at a flow rate of 2.5 mL/min; CAI retention time=6.3 min).

Formulation 5

Formulation 5 is prepared according to the General Procedure described in Example 1 using the following amounts of reagents or corresponding relative proportions: CAI free base (50 mg), oleic acid (150 mg), soybean oil (150 mg), Pluronic® F-127 (100 mg) and Tween®-80 (100 mg). A creamy emulsion of milky white appearance is formed after dilution with water to a final CAI concentration of 36 mg/mL (3.6%). The emulsion of Formulation 4 is stable based on stability to phase separation at ambient temperature. The active CAI ingredient is stable to autoclave sterilization conditions of 121° C. at a pressure of 15 psi as defined in Example 1. Thus, after autoclaving Formulation 5 under these conditions for 30 min no decomposition of CAI or formation of new impurities could be detected by RP-HPLC analysis using UV detection (Conditions: RP-18 column: 5µ particle size, length=13 cm, diameter=8 mm; solvent system: solvent A=0.001% trifluoroacetic acid, solvent B=acetonitrile, gradient=80% A/20% B to 10% A/90% B over 12 min at a flow rate of 2.5 mL/min; CAI retention time=6.3 min).

Formulation 6

Formulation 6 is prepared according to the General Procedure described in Example 1 using the following amounts of reagents or corresponding relative proportions: CAI free base (25 mg), oleic acid (150 mg), soybean oil (150 mg), Pluronic® F-68 (100 mg) and Tween®-80 (100 mg). A creamy emulsion of milky white appearance is formed after dilution with water to a final CAI concentration of 8 mg/mL (0.8%). The emulsion of Formulation 6 is stable based on stability to phase separation at ambient temperature. The active CAI ingredient is stable to autoclave sterilization conditions of 121° C. at a pressure of 15 psi as defined in Example 1. Thus, after autoclaving Formulation 6 under these conditions for 30 min no decomposition of CAI or formation of new impurities could be detected by RP-HPLC analysis using UV detection (Conditions: RP-18 column: 5µ particle size, length=13 cm, diameter=8 mm; solvent system: solvent A=0.001% trifluoroacetic acid, solvent B=acetonitrile, gradient=80% A/20% B to 10% A/90% B over 12 min at a flow rate of 2.5 mL/min; CAI retention time=6.3 min).

Example 2

Intravitreal Injection

Pharmacologically effective concentrations in diverse in vitro and in vivo model systems of CAI at 0.5 to 10 micromolar concentration which is consistent with a dose of 0.2 ng to 40 ng of drug in a compartment of about 4 to 5 mL for the eye for a long term 4 to 6 week maintenance of a controlled dose use with indicate a dose range of 50 ng to 500 ng of CAI active ingredient or greater.

The intravitreal injection would be administered via the inferotemporal pars plana, in a protocol similar to triamcinalone, Macugen®, or Lucentis®. As a single dose of 5 mg of dexamethasone-administered subconjunctivally can reach micromolar concentrations in the subretinal space and vitreous, and CAI possesses similar trans-scleral permeability kinetics, an initial dose of 5 to 50 mg for periocular administration is proposed. An effective quantity of the compound of interest is employed in treatment.

As understood by the skilled clinician, the dosage of compounds used in accordance with the invention varies depending on the compound and the condition being treated. For example, the age, weight, and clinical condition of the recipient patient, and the experience and judgment of the clinician or practitioner administering the therapy are among the factors affecting the selected dosage. Other factors include the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

Example 3

Single Ingredient Formulation

Ingredient Concentration w/v % CAI 0.1 to 2% Monobasic Sodium Phosphate Dihydrate 0.051% Dibasic Sodium Phosphate Dodecahydrate 0.5% Tyloxapol 0.05-0.4% Sodium Chloride 0.76% NaOH/HCl pH adjust to 5.0-8.4 Water for injection q.s. 100%.

Example 4

Steroid Combination Formulation

Ingredient Concentration w/v % CAI 0.1 to 2% Triamcinolone Acetonide 0.5-4.0% Monobasic Sodium Phosphate Dihydrate 0.051% Dibasic Sodium Phosphate Dodecahydrate 0.5% Tyloxapol 0.05-0.4% Sodium Chloride 0.76% NaOH/HCl pH adjust to 5.0-8.4 Water for injection q.s. 100%.

Example 5

Neuroprotective Combination Formulation

Ingredient Concentration w/v % CAI 0.1 to 2% Neuroprotecive agent 0.5-4.0% Monobasic Sodium Phosphate Dihydrate 0.051% Dibasic Sodium Phosphate Dodecahydrate 0.5% Tyloxapol 0.05-0.4% Sodium Chloride 0.76% NaOH/HCl pH adjust to 5.0-8.4 Water for injection q.s. 100%.

Example 6

Chelating Agent Combination Formulation

Ingredient Concentration w/v % CAI 0.1 to 2% Chelating Agent 0.5-4.0% Monobasic Sodium Phosphate Dihydrate 0.051% Dibasic Sodium Phosphate Dodecahydrate 0.5% Tyloxapol 0.05-0.4% Sodium Chloride 0.76% NaOH/HCl pH adjust to 5.0-8.4 Water for injection q.s. 100%.

Example 7

Topical Formulation

A typical example of topical formulation of CAI is as follows: Ingredient Concentration w/v % (Preferred Range) CAI Polyquad 0.0005-0.01% (0.0001%); HPMC (hydroxypropylmethylcellulose) 0.02-1.0% (0.5%); Mannitol (b) 0.0-5.0% (3.82%); Sodium Chloride (d) 0.0-0.8% (0.17%); Disodium Edetate 0.0-0.2% (0.01%); Polysorbate-80 (c) 0.005-0.4% (0.05%); NaOH and/or HCl q.s. pH 5.0-8.4 (6.8-7.8); Purified Water q.s. 100%. (a) Other suitable polymers include cellulosic polymers like HPMC, HEC (hydroxyethylcellulose), sodium CMC (sodium carboxymethylcellulose), polyvinyl alcohol (PVA), Polyvinyl Pyrrolidone (PVP), polyacrylamide, and other water miscible/soluble polymers to impart viscosity to the product and to stabilize suspension. (b) Both ionic as well nonionic agents are used to adjust Osmolality of the product either alone or in combination. This also stabilizes the suspension. (c) Other surfactants that can be used are non-ionic (Tyloxapol, Tweens, Spans) anionic (lecithin, hydrogenated lecithins), or anionic (sodium lauryl sulfate, bile salts).

The following contemplated clinical cases of angiogenesis are presented as examples of methods of treatment and not as limitations. Other illustrations of treating systemic or localized angiogenesis are not presented, since the principles involved are similar, and will be apparent to the skilled reader based upon review of an individual's clinical manifestation and the preferred embodiments of the inventive compositions.

Example 8

Diabetic Complications

Patient A is determined to be experiencing an acute relapse of diabetes, e.g., diabetic coma. Patient A has a history of diabetes over the past 20 years, with increasing debilitation from progressive diabetic retinopathy, nephropathy, and neuropathy. Patient A has not yet had panretinal laser photocaogulopathy but has been treated with focal laser for macular edema. Retinal examination reveals Patient A has not progressed to threshold criteria for panretinal photocoagulation per the Diabetic Retinopathy Study (DRS) guidelines.

According to the subject invention, Patient A will require scheduling of a follow-up visit and low-dose treatment with a CAI compound of the invention in an attempt to delay or remove the need for panretinal laser photocoagulopathy. Patient A is given a direct intravitreal injection of a high dose of CAI, 50 microgram/injection every week for 4 weeks. The dose remains constant with weekly injections and Patient A is scheduled for panretinal laser photocoagulopathy with continued weekly retinal examination follow-up to determine disease course and confirm necessity for panretinal laser photocoagulopathy.

After regression of the neovascularization, Patient A is treated with focal laser therapy for macular edema, if needed, and provided a with monthly, or less frequent, intravitreal injections of CAI with the administration frequency and dose adjusted according to patients clinical manifestations and to maintain neovascular regression. Intravitreal injections may be supplemented or replaced by other appropriate routes of administration and this could be dictated by the patients clinical presentation, health, expected treatment compliance profile, and appropriateness of local, systemic, or controlled release treatment. CAI treatment would be targeted to be tapered off to prophylactic systemic or controlled release therapy, as the condition improves sufficiently.

Patient B is also determined to be experiencing an acute relapse of diabetes, e.g., diabetic coma and has a history of diabetes over the past 20 years, with increasing debilitation from progressive diabetic retinopathy, nephropathy, and neuropathy. Patient B has not yet had panretinal laser photocoagulopathy nor has she been treated with focal laser for macular edema. Patient B has not developed threshold proliferative diabetic retinopathy. This patient is clinically similar to Patient A, but the evidence of no macula involvement obviates the need for scheduling focal laser photocoagulation.

According to the subject invention, Patient B is given a direct intravitreal injection of a low dose of CAI, 5 microgram/injection. The dose remains constant with a second intravitreal injection 4 weeks later. Patient B is followed clinically every 3 months and treated with focal laser therapy, if needed, or provided with subsequent intravitreal injections of CAI with the administration frequency and dose adjusted according to Patient B's clinical manifestations. Intravitreal injections may be supplemented or replaced by other appropriate routes of administration and this could be dictated by the patients clinical presentation, health, expected treatment compliance profile, and appropriateness of local, systemic, or controlled release treatment. CAI treatment is targeted as prophylactic systemic or controlled release therapy, if the condition improves sufficiently.

Example 9

Proliferative Diabetic Retinopathy 62-year old male with Proliferative Diabetic Retinopathy and threshold high-risk characteristics presents with Vitreous Hemorrhage. The patient also has atrial fibrillation and ischemic cardiomyopathy that requires oral Coumadin. The patient is intolerant to topical Panretinal Photocoagulation. The INR measured at just less than 2. Because of this acute event intravitreal injection, a medium dose of 50 mcg CAI is administered with some neovascular regression. The patients Vitreous Hemorrhage slowly resolves and the patient is able to taper his Coumadin so that Panretinal Photocoagulation can be placed with retrobulbar anesthesia. Alternately, the patient remains on Coumadin and then is treated with a patch periocular insert of CAI to diminish the neovascularization.

Example 10

Central Scotoma Treatment Complications 78-year old woman with a two-week history of central scotoma. She developed a large disciform scar in the contralateral eye after several sessions of photodynamic therapy. On exam and fluorescein angiography is predominately classic subfoveal membrane is noted. Intravitreal injection of a high dose, 200 mcg, CAI is given to hasten the neovascular regression. After this high dose of intravitreal CAI a periocular injection of CAI in a sustained-release solution is given and neovascular regression occurs.

Example 11

Age-Related Macular Degeneration Complication 67-year old white male who has had three years of poor vision secondary to a disciform scar associated with Age-Related Macular Degeneration. He has high-risk drusen and parafoveal pigmentation. A long acting low dose subconjunctival or periocular implant of CAI 1 mg is affixed to the well-sighted eye to prophylax against neovascularization.

Example 12

Glaucoma Complication 82-year old woman with low-tension glaucoma. She has a history of hypotony maculopathy in the left eye after trabeculectomy with visual acuity loss to 20/200 secondary to hypotony maculopathy associated with an intraocular pressure of 7 to 8. In the right eye, she is progressively cupping with a Cup/Disc ratio 0.85 despite maximal medical treatment and an intraocular pressure of 11. A low dose 1 mg periocular insert for injection of CAI is given in order to maximize neuroprotection.

Example 13

Proliferative Diabetic Retinopathy 28-year old noncompliant diabetic male who initially presented with aggressive Proliferative Diabetic Retinopathy. Heavy and full Panretinal Photocoagulation was performed, however there is recurrent residual Vitreous Hemorrhaging from a small active frond of neovascularization that is within heavy Panretinal Photocoagulation scars. An intravitreal injection of moderate dose, 100 mcg of CAI is given to cause neovascular involution and the patient is maintained with a moderate dose of 10 mg administered by periocular injection of CAI in a sustained-release solution.

Example 14

Proliferative Diabetic Retinopathy 37-year old white male who is with Proliferative Diabetic Retinopathy and has undergone Trans Pars Plana Vitrectomy x's 2 for Vitreous Hemorrhage. He has a heavy pattern of Panretinal Photocoagulation scars and it is thought that he has neovascularization arising from the sclerotomy sites, and/or the pars plana, which is causing persistent hemorrhage. A high dose of 200-mcg dose of CAI is administered intravitreally and then two weeks later an outpatient air-fluid exchange is performed, and a moderate dose, periocular injection of 10 mg of CAI is given to prevent further Vitreous Hemorrhage.

Example 15

Vision Loss 16-year old female who presents with a several month history of vision loss and is found to have a large angiomatous lesion that is causing a subtotal retinal detachment. Secondary to the lesion size it is not amenable for cryotherapy and standard laser photocoagulation. Initially a high dose of 200 mcg CAI is given intravitreally and two weeks later a periocular insert is placed of 10 mg, moderate dose of CAI onto the sclera overlying the lesion.

Example 16

Central Retinal Vein Occlusion 66-year old male who presents with a Central Retinal Vein Occlusion and florid Iris Neovascularization with Neovascular Glaucoma. As an adjunct to Panretinal Photocoagulation secondary to the florid neovascular activity, a high dose of 200 mcg CAI is given as a synergistic measure to cause regression of the anterior segment neovascularization and normalization of the pressure.

Example 17

Iris and Preretinal Neovascularization 39-year old white male strikes his head on a laboratory cabinet. This causes a chronic peripheral retinal detachment with iris neovascularization and preretinal neovascularization. In order to decrease the risk of intraocular hemorrhage and glaucoma associated with retinal reattachment, a moderate dose of 100 mcg of CAI is given intravitreally and one-week later successful retinal reattachment surgery is performed.

Example 18

Proliferative Sickle Cell Retinopathy 40-year old male with a history of Traction Retinal Detachment and vision loss in one eye from proliferative sickle cell retinopathy. The patient developed a Vitreous Hemorrhage in the fellow and has only incomplete regression following peripheral scatter laser. Relatively low dose CAI 1 mg is administered periocularly to cause involution of the small amount of residual neovascularization which is causing persistent Vitreous Hemorrhage.

Example 19

Choroidal Neovascular Membrane Complications 44-year old white male with a history of Choroidal Neovascular Membrane secondary to high myopia. One eye has Fuch's spots and 20/200 vision. The second eye is affected with a subfoveal Choroidal Neovascular Membrane and 20/80 vision. A single injection of moderate dose, 100 mcg, of CAI is administered intravitreally to hasten neovascular regression.

Example 20

Photodynamic Therapy Complications 32-year old female with multifocal choroiditis and macular scarring in one eye after several sessions of Photodynamic Therapy. She presents in the second eye with decreased vision and a subfoveal Choroidal Neovascular Membrane. A mixture of 4 mg of Kenalog, and a high dose of 200 mcg of intravitreal CAI are administered to hasten neovascular regression.

Example 21

Treatment of Posterious Infectious Uveitis 35-year old female with posterior infectious uveitis. She presents symptoms of posterior infectious uveitis due to a parasitic infection. A sustained time-release polymeric implant of 150 to 200 mcg of CAI and of about 0.7 mg dexamethasone is implanted or injected into the inside of the eye.

Example 22

Treatment of Posterious Infectious Uveitis 78-year old male with posterior infectious uveitis and endophthalmitis following four days after cataract surgery. He presents symptoms of posterior infectious uveitis due to a parasitic infection. A sustained time-release polymeric implant of 150 to 200 mcg of CAI with an antibacterial agent or agents and a glucocorticoid is implanted or injected into the inside of the eye. The sustained time-release implant may be designed to dissolve.

It should be understood that the embodiments of the invention shown and described in the specification are only preferred embodiments of the inventor who is skilled in the art and are not limiting in any way. Therefore, various changes, modifications, or alterations to these embodiments may be made or resorted to without departing from the spirit of the invention and the scope of the following claims. While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

What is claimed is:

1. A method of treating parasite induced posterior infectious uveitis in a patient comprising administering to the patient a sustained-release system comprising a pharmaceutically effective amount of 5-amino-[4-(4-chlorobenzoyl)-3,5-dichlorobenzyl]-1,2,3-triazole-4-carboxamide) (CAI).

2. The method of claim 1, wherein the sustained-release system comprises a polymer.

3. The method of claim 2, wherein the polymer degrades over time.

4. The method of claim 3, wherein the polymer comprises polylactic-coglycolic acid (PLGA).

5. The method of claim 1, wherein the sustained release system comprises a non-erodible intravitreal implant.

6. The method of claim 1, wherein the posterior infectious uveitis is caused by toxoplasmosis, *toxocara* or visceral larva migrans.

7. The method of claim 1, wherein the sustained-release system further comprises one or more of an anti-inflammatory agent, a steroid and/or an antibacterial agent.

8. The method of claim 7, wherein the steroid is a glucocorticoid or fluocinolone acetonide.

9. The method of claim 8, wherein the glucocorticoid comprises dexamethasone.

10. The method of claim 1, wherein CAI is a sonicated microparticle or in a molecular complex in formulation with hydroxypropyl β-cyclodextrin.

11. A method of treating parasite induced posterior infectious uveitis in a patient comprising administering a sustained-release system comprising a pharmaceutically effective amount of 5-amino-[4-(4-chlorobenzoyl)-3,5-dichlorobenzyl]-1,2,3-triazole-4-carboxamide) and a steroid to a patient.

12. The method of claim 11, wherein the steroid is a glucocorticoid or fluocinolone acetonide.

13. The method of claim 11, wherein the sustained-release system comprises a polymer.

14. The method of claim 13, wherein the polymer comprises polylactic-coglycolic acid (PLGA).

15. The method of claim 11, wherein the steroid comprises dexamethasone.

16. The method of claim 11, wherein the sustained-release system further comprises an anti-inflammatory agent and/or an anti-bacterial agent.

17. The method of claim 13, wherein the polymer degrades over time.

18. The method of claim 11, wherein CAI is a sonicated microparticle or in a molecular complex in formulation with hydroxypropyl β-cyclodextrin.

19. The method of claim 11, wherein the sustained release system comprises a non-erodible intravitreal implant.

20. The method of claim 11, wherein the posterior infectious uveitis is caused by toxoplasmosis, *toxocara* or visceral larva migrans.

21. The method of claim 9, wherein the amount of dexamethasone is from about 0.5 to about 0.9 mg.

\* \* \* \* \*